United States Patent
Henderson et al.

(10) Patent No.: US 6,406,861 B1
(45) Date of Patent: Jun. 18, 2002

(54) METHODS OF ENHANCING EFFECTIVENESS OF THERAPEUTIC VIRAL IMMUNOGENIC AGENT ADMINISTRATION

(75) Inventors: Daniel R. Henderson, Palo Alto; Yu Chen, Sunnyvale; De Chao Yu, Foster City, all of CA (US)

(73) Assignee: Cell Genesys, Inc., Foster City, CA (US)

( * ) Notice: Subject to any disclaimer, the term of this patent is extended or adjusted under 35 U.S.C. 154(b) by 0 days.

(21) Appl. No.: 09/413,044

(22) Filed: Oct. 6, 1999

Related U.S. Application Data

(60) Provisional application No. 60/103,445, filed on Oct. 7, 1998.

(51) Int. Cl.[7] .................. G01N 33/53; A61K 39/00; A61K 39/23; A61K 39/42; A61K 39/395
(52) U.S. Cl. ............... 435/7.1; 424/140.1; 424/233.1; 424/131.1; 424/159.1; 424/278.1; 424/93.1; 530/351; 514/885
(58) Field of Search ............... 435/7.1; 424/140.1, 424/233.1, 131.1, 159.1, 278.1, 93.1; 530/351; 514/885

(56) References Cited

U.S. PATENT DOCUMENTS

| | | | |
|---|---|---|---|
| 4,086,294 A | 4/1978 | Koleske et al. | 260/834 |
| 4,233,672 A | 11/1980 | Suzuki et al. | 365/181 |
| 4,255,627 A | 3/1981 | Marquis | 200/38 R |
| 4,411,792 A | 10/1983 | Babb | 210/651 |
| 4,551,435 A | 11/1985 | Liberti et al. | 436/541 |
| 4,643,718 A | 2/1987 | Marten | 604/28 |
| 4,762,787 A | 8/1988 | Balint | 435/174 |
| 4,851,126 A | 7/1989 | Schoendorfer | 210/651 |
| 5,122,112 A | 6/1992 | Jones | 604/4 |
| 5,147,290 A | 9/1992 | Jonsson | 604/5 |
| 5,652,224 A | 7/1997 | Wilson et al. | 514/44 |
| 5,733,254 A | 3/1998 | Jones et al. | 604/4 |

FOREIGN PATENT DOCUMENTS

| | | |
|---|---|---|
| WO | WO 97/17980 A1 | 5/1997 |
| WO | WO 98/04132 A1 | 2/1998 |
| WO | WO 98/39464 A2 | 9/1998 |
| WO | WO 98/39467 A2 | 9/1998 |
| WO | WO 99/06575 A1 | 2/1999 |

OTHER PUBLICATIONS

Gahéry–Ségard, H. et al. (1998). "Immune Response to Recombinant Capsid Proteins of Adenovirus in Humans: Antifiber and Anti–Penton Base Antibodies Have a Synergistic Effect on Neutralizing Activity," *J. Virol.* 72(3):2388–2397.

Shariff, D.M. et al. (1988). "Immune Inhibition of Virus Release from Herpes Simplex Virus–Infected Cells by Human Sera," *Intervirology* 29(3):125–132.

(List continued on next page.)

*Primary Examiner*—Hankyel T. Park
*Assistant Examiner*—Stacy S. Brown
(74) *Attorney, Agent, or Firm*—Pamela J. Sherwood; Bozicevic, Field & Francis LLP

(57) ABSTRACT

Methods of reducing pre-existing humoral immunity to a viral immunogenic therapeutic agent such as adenovirus, using immunoapheresis are disclosed. Antibodies specific for the viral immunogenic therapeutic agent are selectively removed from the blood of an individual prior to administration of the viral immunogenic therapeutic agent by reaction extracorporeally with an immunosorbent which specifically binds the antibody. After the antibody is selectively removed from the blood, the blood is reinfused into the patient and the viral immunogenic therapeutic agent is administered. The invention also provides kits and compositions for selective removal of anti-viral antibody.

26 Claims, 25 Drawing Sheets

OTHER PUBLICATIONS

Arnberg et al. (1997). "Fiber genes of adenoviruses with tropism for the eye and the genital tract," *Virology* 277:239–244.

Bandarenko. (1996). "Apheresis: new opportunities," *Clinics in Laboratory Medicine* 16:907–929.

Berkner. (1983). "Generation of adenovirus by transfection of plasmids," *Nucl. Acids Res.* 11(17):6003–6020.

Bett et al. (1993). "Packaging capacity and stability of human adenovirus type 5 vectors," *Virology* 67(10):5911–5921.

Bett et al. (1994). "An efficient and flexible system for construction of adenovirus vectors with insertions or deletions in early regions 1 and 3," *Proc. Natl. Acad. Sci. USA* 91:8802–8806.

Bischoff et al. (1996). "An adenovirus mutant that replicates selectively in p53–deficient human tumor cells," *Science* 274:373–376.

Bramson et al. (1997). "Pre–existing immunity to adenovirus does not prevent tumor regression following intratumoral administration of a vector expressing IL–12 but inhibits virus dissemination," *Gene Therapy* 4: 1069–1076.

Browne et al. (1993). "Analysis of protective immune responses to the glycoprotein H–glycoprotein L complex of herpes simplex virus type 1," *J. Gen. Virol.* 74:2813–2817.

Christ et al. (1997). "Gene therapy with recombinant adenovirus vectors: evaluation of the host immune response," *Immunol. Lett.* 57:19–25.

Christie et al. (1993). "Treatment of refractoriness to platelet transfusion by protein A column therapy," *Transfusion* 33(3):234–242.

Chroboczek et al. (1992). "The sequence of the genome of adenovirus type 5 and its comparison with the genome of adenovirus type 2," *Virology* 186:280–285.

Cohen et al. (1992). "Structural and functional studies of herpes simplex virus glycoprotein D," in *Genetically Engineered Vaccines*, Ciardi et al. ed., Plenum Press: New York, pp. 217–228.

Durali et al. (1988). "Cross–reactions between the cytotoxic t–lymphocyte responses of human immunodeficiency virus–infected African and European patients," *Virology* 72(5):3547–3553.

Eing et al. (1989). "Neutralizing activity of antibodies against the major herpes simplex virus 1 glycoproteins," *J. Med. Virol.* 27(1):59–65.

Felgner et al. (1989). "Cationic liposome–mediated transfection," *Nature* 337: 387–388.

Fisher et al. (1997). "Recombinant adeno–associated virus for muscle directed gene therapy," *Nat. Med.* 3(3):306–312.

Gahéry–Ségard et al. (1997). "Humoral immune response to the capsid components of recombinant adenoviruses: routes of immunization modulate virus–induced Ig subclass shifts," *Eur. J. Immunol.* 27:653–659.

Gahéry–Ségard et al. (1997). "Phase I trial of recombinant adenovirus gene transfer in lung cancer," *J. Clin. Invest.* 100(9):2218–2226.

Garon et al. (1972). "A unique form of terminal redundancy in adenovirus DNA molecules," *Proc. Natl. Acad. Sci. USA* 69(9):2391–2395.

George–Fries et al. (1984). "Analysis of proteins, helper dependence, and seroepidemiology of a new human parvovirus," *Virology* 134(1):64–71.

Graham. (1984). "Covalently closed circles of human adenovirus DNA," *EMBO J.* 3(12):2917–2922.

Guéérette et al. (1996). "Prevention of immune reactions triggered by first–generation adenoviral vectors by monoclonal antibodies and CTLA4Ig," *Hum. Gene Ther.* 7:1455–1463.

Heise et al. (1997). "ONYX–015, an E1B gene–attenuated adenovirus, causes tumor specific cytolysis and antitumoral efficacy that can be augmented by standard chemotherapeutic agents," *Nat. Med.* 3:639–645.

Highlander et al. (1987). "Neutralizing monoclonal antibodies specific for herpes simplex virus glycoprotein D inhibit virus penetration," *Virology* 61(11):3356–3364.

Hioe et al. (1997). "Neutralization of HIV–1 primary isolates by polyclonal and monoclonal human antibodies," *Int. Immun.* 9(9): 1281–1290.

Horowitz. (1990). "Adenoviridae and their replication," Chapter 60 in *Virology*, Fields et al. ed., Raven Press: New York, 2nd ed., pp. 1679–1721.

Ilan et al. (1997). "Oral tolerization to adenoviral antigens permits long–term gene expression using recombinant adenoviral vectors," *J. Clin, Invest.* 99(5):1098–1106.

Kay et al. (1995). "Long–term hepatic adenovirus–mediated gene expression in mice following CTLa4Ig administration," *Nature Gen.* 11:191–197.

Kirn et al. (1996). "Replicating viruses as selective cancer therapeutics," *Mol. Med. Today* 12:519–527.

Maizel et al. (1968). "The polypeptides of adenovirus," *Virology* 36:115–125.

Molnar–Kimber et al. (1998). "Impact of preexisting and induced humoral and cellular immune responses in an adenovirus–based gene therapy phase I clinical trial for localized mesothelioma," *Hum. Gene Ther.* 9:2121–2133.

Nilsson et al. (1981). "A procedure for removing high titer antibodies by extracorporeal protein–A–sepharose adsorption in hemophilia: substitution therapy and surgery in a patient with hemophilia B and antibodies," *Blood* 58(1):38–44.

Pascher et al. (1997). "Application of immunoapheresis for delaying hyperacute rejection during isolated xenogenic pig liver perfusion," *Transplantation* 63(6):867–875.

Pring–Akerblom et al. (1995). "Hexon sequence of adenovirus type 7 and comparison with other serotypes of subgenus B," *Res. Virol.* 146(6):383–388.

Reubel et al. (1997). "Identification, cloning and sequence analysis of the equine adenovirus 1 hexon gene," *Arch. Virol.* 142(6):1193–1212.

Richter et al. (1993). "Three–year treatment of familial heterozygous hypercholesterolemia by extracorporeal low–density lipoprotein immunoadsorption with polyclonal apolipoprotein B antibodies," *Metabol. Clin. Exp.* 42(7):888–894.

Richter et al. (1997). "Efficacy and safety of immunoglobin apheresis," *ASAIO J.* 43(1):53–59.

Rutledge et al. (1998). "Infectious clones and vectors derived from adeno–associated virus," *Virology* 72(1):309–319.

Sanchez–Pescador et al. (1993). "Antibodies to epitopes of herpes simplex virus type 1 glycoprotein B (gB) in human sera: analysis of functional gB epitopes defined by inhibition of murine monoclonal antibodies," *J. Infec. Dis.* 168(4):844–853.

Sawchuck et al. (1996). "Anti–t cell receptor monoclonal antibody prolongs transgene expression following adenovirus–mediated In Vivo gene transfer to mouse synovium," *Hum. Gene Ther.* 7:299–506.

Schulik et al. (1997). "Established immunity precludes adenovirus–mediated gene transfer in rat carotid arteries," *J. Clin. Invest.* 99(2):209–219.

Shields et al. (1985). "Adenovirus infections in patients undergoing bone–marrow transplantation," *New Engl. J. Med.* 312(9):529–533.

Smith et al. (1996). "Transient immunosuppression permits successful repetitive intravenous administration of an adenovirus," *Gene Therapy* 3:496–502.

Snyder et al. (1992). "Experience with protein A–immunoadsoprtion in treatment–resistant adult immune thrombocytopenic purpura," *Blood* 79(9): 2237–2245.

Snyder et al. (1993). "Treatment of cancer chemotherapy–associated thrombotic thrombocytopenic purpura/hemolytic uremic syndrome by protein A immunoadsorption of plasma," *Cancer* 71(5):1882–1892.

Suzuki et al. (1994). "Preferential adsorption of cationic anti–DNA antibodies with immobilized polyanionic compounds, dextran sulfate," *Autoimmunity* 19:105–112.

Suzuki et al. (1995). "Evaluation of double filtration plasmapheresis, thermofiltration, and low–density lipoprotein adsorptive methods by crossover test in treatment of familial hypercholesterolemia patients," *Artificial Organs* 20(4):296–302.

Vestergaard. (1980). "Herpes simplex virus antigens and antibodies: a survey of studies based on quantitative immunoelectrophoresis," *Rev. Infect. Dis.* 2(6):899–913.

Wallukat et al. (1996). "Removal of autoantibodies in dilated cardiomyopathy by immunoadsorption," *Int'l J. Card.* 54:191–195.

Watson et al. (1989). "Casplatin–associated hemolytic–uremic syndrome," *Cancer* 64(7):1400–1403.

Weber et al. (1994). "Sequence and structural analysis of murine adenovirus type 1 hexon," *J. Gen. Virol.* 75:141–147.

Worgall et al. (1997). "Innate immune mechanisms dominate elimination of adenoviral vectors following In Vivo administration," *Hum. Gene Ther.* 8:37–44.

Yang et al. (1995). "Cellular and humoral immune responses to viral antigens create barriers to lung–directed gene therapy with recombinant adenoviruses," *Virology* 69(4):2004–2015.

Zahradnik et al. (1980). "Adenovirus infection in the immunocompromised patient," *Am. J. Med.* 68:725–732.

Zinkernagel. (1996). "Immunology taught by viruses," *Science* 271:173–178.

METHODS OF ENHANCING EFFECTIVENESS OF THERAPEUTIC VIRAL IMMUNOGENIC AGENT ADMINISTRATION

CROSS-REFERENCE TO RELATED APPLICATIONS

This application claims the priority benefit of provisional U.S. Patent Application No. 60/103,445, filed Oct. 7, 1998, pending, which is hereby incorporated herein by reference in its entirety.

STATEMENT OF RIGHTS TO INVENTIONS MADE UNDER FEDERALLY SPONSORED RESEARCH

Not applicable.

1. Technical Field

This invention relates to the field of administration of viral immunogenic therapeutic agents, particularly diminishing host humoral immune response to such administration.

2. Background Art

A broad spectrum of human disease involves genetic aberrations at the cellular level. Some of these diseases include cystic fibrosis, anemia, hemophilia, diabetes, Huntington's Disease, AIDS, abnormally high serum cholesterol levels, and certain immune deficiencies. In particular, a disease that has touched almost everyone's lives is cancer. In spite of massive research efforts, only limited progress has been made in treating any of these diseases.

A number of new potentially promising therapies are currently under development. Gene therapy, in which a defective gene or sequence is supplanted with an exogenenous sequence, may be useful in treating not only cancer, but all of the previously listed diseases. Gene therapy generally requires a delivery vehicle for the exogenous sequence such as a viral vector. Newly developed viral agents that may be effective vectors against these diseases include retroviruses and recombinant adenoviruses. For review see Kim et al. (1996) *Mol. Med. Today* 12:519–527) and Smith et al. (1996) *Gene Therapy* 3:496–502. Other viral vectors that are potentially useful as therapeutic agents include Moloney mouse leukemia virus (MoMLV), Pox virus, Herpes virus, HIV and Adeno-associated viruses (AAV).

In addition, in the cancer context, more specific attenuated replication competent viral vectors have been developed, in which selective replication in cancer cells preferentially destroys those cells. Various cell specific replication competent adenovirus constructs, which preferentially replicate (and thus destroy) certain cell types, are described in commonly-owned U.S. patent application Ser. Nos. 09/033,555, 09/033,333, 60/076,545, and 09/033,556. Another attenuated replication-competent adenovirus is Onyx-015 adenovirus. Onyx-015 has a deletion in the E1B-55 kDa protein, which normally inhibits the cellular p53 tumor suppressor protein. Onyx-015 can replicate in p53-deficient human cells, but does not replicate efficiently in p53-positive cells. Bischoff et al. (1996) *Science* 274:373–376; Heise et al. (1997) *Nat. Med.* 3:639–645.

The favorable factors contributing to adenovirus as a safe therapeutic agent include: (a) infection with adenovirus has minor clinical disease manifestations; (b) adenovirus has a stable well-described and characterized genome; (c) adenovirus is unable to integrate its viral DNA into host DNA; (d) adenovirus allows transient gene expression; (e) adenovirus is able to infect both dividing and non-dividing cells; (f) adenovirus can infect a variety of human cell types; (g) adenovirus is physically stable, and (h) adenovirus is amenable to high titer production.

The adenovirus type 5 genome is a double-stranded DNA molecule of 35,935 base pairs containing short inverted terminal repeats. Chroboczek et al. (1992) *Virology* 186:280–285; Garon et al. (1972) *Proc. Natl. Acad. Sci. USA* 69:2391–2395. Expression of the genome is a regulated cascade which is arbitrarily divided into early (E) and late (L) phases, with viral DNA replication required for maximal L gene expression. Related RNA transcripts are grouped according to the region of the genome from which they are transcribed as well as by the timing (E or L) of their expression. The E3 region is not essential for replication in tissue culture and this region is deleted from most first-generation therapeutic adenovirus.

There are 47 different serotypes of adenovirus, which are distinguishable by antibody reactivity to epitopes on the virion surface. Each serotype is assigned to one of five Subgroups (A–E). Members of a Subgroup can exchange genetic material (recombine) efficiently, but they do not recombine with members of a different Subgroup. Adenovirus types 1, 2, 5, and 6 are members of Subgroup C. Adenovirus type 5 (the type typically used in gene therapy and for other therapies) is associated with a self-limiting, febrile respiratory illness and ocular disease in humans. In long-term immunosuppressed individuals, adenovirus 5 is also associated with renal impairment, hepatic necrosis, and gastric erosions. Shields et al. (1985) *New England J. Med.* 312:529–533; Zahradnik et al. (1980) *Am. J. Med.* 68: 725–732. Adenovirus 5 and the other Subgroup C viruses have little or no oncogenic potential in mammals. Horowitz (1990) in *Virology*, (Raven Press, New York, $2^{nd}$ Ed.) pp. 1679–1721.

Use of viral therapeutic agents such as adenovirus holds promise, but there are a number of significant barriers to their effectiveness. Two of the major limitations of virus-based vectors as therapeutic vehicles are (a) the inactivation of virus by pre-existing circulating antibodies to the virus, and (b) the reduced efficacy of repeat dosage by primary or secondary induction of humoral immunity. For example, with respect to adenovirus, a recent serological survey indicates that 57% of the adult population in the U.S. has neutralizing antibodies to adenovirus 5 with titers ranging from 1:2 to 1:512. Schulick et al. (1997) *J. Clin. Invest.* 99:209–219. Neutralizing antibodies are generated to specific antigenic determinants within 7–14 days following intravenous adenovirus injection. Zinkernagel (1996) *Science* 271:173–178. These antibodies are typically specific for proteins on the virion, such as capsid proteins and various glycoproteins. George-Fries et al (1984) *Virology* 134(1):64–71; Fisher et al. (1997); Eing et al. (1989) *J. Med. Virol.* 27(1):59–65; Highlander et al. (1987) *J. Virol.* 61(11) 3356–64; Durali et al. (1998) *J. Virol.* 72(5):3547–53. Activation of CD4+ lymphocytes by adenovirus capsid proteins also leads to the up-regulation of MHC class I molecules in infected cells contributing to the production of neutralizing antibodies as well as the clearing of adenovirus infected cells by CTLs. Yang et al. (1995) *J. Virol.* 69:2004–2015. For many patients, a therapeutic adenovirus will elicit an amnestic humoral response and a CTL response further decreasing the efficacy of repeat intravenous treatment with the same virus. Since the majority of the human population has been exposed to adenovirus during their lifetime, pre-existing immunity could be a major obstacle to the use of viral vectors. Such high prevalence of neutralizing antibodies to adenovirus in adult humans could inhibit adenovirus dissemination (to distant tumor sites for example) and greatly limit the effectiveness of adenovirus type 5-based therapy in vivo.

The effect of neutralizing antibodies on viral dissemination is a major issue in determining the success of viral therapy using parenteral administration, especially since intravenous administration may be desirable for treatment for metastatic disease or non-discrete tumors. Although recent studies have indicated that pre-existing antibody may not reduce the efficiency of intratumoral viral administration (in terms of tumor regression), virus dissemination appears to be greatly impeded by pre-existing circulating antibodies. One group found that transgene expression in the liver of adenovirus-immune animals following intratumoral injection was reduced more than 1000-fold compared to the transgene expression found in naive mice. Bramson et al. (1997) *Gene Therapy* 4:1069-1-76. In another example, in mice 90% of viral vectors is eliminated within 24 hours of intravenous injection. Worgall et al. (1997) *Hum. Gene Ther.* 8:37–44. This finding was confirmed by quantitative analysis of viral DNA in liver, spleen and lung using Southern analysis over the first 70 hours post injection demonstrating a 90% elimination of vector. Christ et al. (1997) *Immunology Letters* 57:19–25. Schulick et al. (1997) found if rats are immunized by prior intravenous exposure to adenovirus, a second intravenous injection of an adenovirus vector gave no evidence of recombinant gene expression three days after the attempted gene transfer. This observation could be reproduced even in the presence of low (i.e., 1:2) titers of neutralizing antibody to adenovirus. Schulick et al. (1997). Another group examined immune responses to an adenoviral vector and to the recombinant gene expression (β-galactosidase protein) in four patients with lung cancer. Gahery-Segard et al. (1997) *J. Clin. Invest.* 100:2218–2226. In patient 1, a high level of neutralizing antibodies to adenovirus was detected before adenovirus-β-gal injection (100% neutralization at 1:400), whereas it was low in patient 3 (30% neutralization at 1:400) and undetectable in the other two patients. Virus DNA was detected by PCR in tumor biopsies on day 30 and day 60 from all patients except patient 1. Thus, Recent studies have established that pre-existing humoral immunity poses a significant barrier to viral half-life, dissemination, and effectiveness and pre-existing anti-adenovirus neutralizing antibodies limit the therapeutic efficacy of adenovirus-mediated therapy through intravenous administration.

Strategies developed to address the problem of pre-existing immunity have significant limitations. Recently, a strategy has been developed for down-regulating pre-existing anti-adenovirus immunity by oral tolerization based on administration of adenoviral proteins. Ilan et al. (1997) *J. Clin. Invest.* 99(5): 1098–1106. But this strategy is not realistic, mostly due to the fact that this method is effective only in newborns.

Apheresis is a process by which certain blood components are removed extracorporeally and the blood is reintroduced into an individual. Typically apheresis is used to treat pathological conditions in which the component to be removed is associated with a particular disease state. Therapeutic apheresis procedures can rapidly remove abnormal blood cells or plasma constituents, and has been used to treat a number of hematologic diseases, including hyperleukocytic leukemias, lymphomas, thrombocythemia, thrombotic thrombocytopenic purpura, sickle cell anemia, and disorders associated with pathologic protein in plasma. The specific procedure could be chosen according to the blood element being removed: cytapheresis, for any blood cell removed; leukapheresis, lymphapheresis, erythrocytapheresis, plateletpheresis (thrombocytapheresis), plasma exchange (therapeutic plasmapheresis), and immunoapheresis. See, e.g., U.S. Pat. Nos. 4,851,126, 4,255,627, 4,086,294, 5,147,290, and 4,411,792.

Recently, affinity adsorption apheresis has been developed for treatment of autoimmune disorders such as hemophilia, idiopathic thrombocytopenia purpura, and lupus nephritis. Nilsson et al. (1981) *Blood* 58(1):38–44; Christie et al. (1993) *Transfusion* 33:234–242; Richter et al. (1997) *ASAIO J.* 43(1):53–59; Suzuki et al. (1994) *Autoimmunity* 19: 105–112; U.S. Pat. No. 5,733,254. ITP is generally characterized by the appearance of lesions resulting from hemorrhage into the skin, a decreased platelet count, increased megakaryocytes in the bone marrow and increased platelet-association IgG in the absence of drug exposure or toxic exposure. The most commonly used column is the staphylococcus protein A column with protein A as the ligand attached to the silica carrier. However, these columns adsorb immunoglobulin generally (with greatest affinity for IgG subclasses 1, 2, and 4, and lower affinity for IgG 3, IgM, and IgA) and immune complexes. Bandarenko (1996) *Clinics in Laboratory Medicine* 16:907–929. The PROSORBA® column (IMRÉ, Inc., San Diego, Calif.) contains protein A linked to silica and is approved for clinical use in the treatment of idiopathic thrombocytopenia purpura (ITP) and HIV-related ITP. Snyder et al. (1992) *Blood* 79:2237–2245; Christie and Howe (1993) *Transfusion* 33:234–242. Another significant limitation of commercially available Protein A columns (besides their relative non-specificity) is their limited binding capacity. Christie et al. (1993). An alternative approach involves the use of columns containing polyclonal anti-human IgG antibodies. Richter et al. (1993) *Metabol. Clin. Exp.* 42:888–894; Richter et al. (1997) *ASAIO J.* 43(1):53–59. However, these columns remove any IgG molecules and are thus not specific.

Other approaches have utilized THERASORB® (formerly manufactured by Baxter Corp, Munich, Germany) columns which was a general affinity column for conjugating an immunosorbent such as antibody. In a model of liver transplantation rejection, a more complete removal of IgG (95%) was found with the use of THERASORB® columns consisting of sheep-anti-human IgG antibodies covalently coupled to Sepharose CL-4B. Pascher et al. (1997) *Transplantation* 63(6):867–875. THERASORB® linked with antibodies against $\beta_1$-adrenoreceptor antibodies was also used in the removal of autoantibodies in another study treating idiopathic dilated cardiomyopathy. Immunoapheresis resulted in an autoantibody level to 8% of original values. Wallukat et al. (1996) *Int'l J. Card.* 54:191–195.

Other experimental applications of affinity apheresis include: the depletion of anti-factor VIII antibodies in the management of hemophilia (Nilsson et al. (1981) *Blood* 58:38; Watson et al. (1989) *Cancer* 64:1400); the removal of cationic anti-DNA antibodies associated with lupus nephritis with polyanionic compounds immobilized on a cellulose column (Suzuki et al. (1994) *Autoimmunity* 19:105–112); the depletion of low-density lipoprotein (LDL) from patients with familial hypercholesterolemia by linking anti-apolipoprotein B to Sepharose (Richter et al. (1993) *Metabol. Clin. Exp.* 42: 888–894; Suzuki et al. (1995) *Artificial Organs* 20(4):296–302); the removal of anti-basement membrane antibodies in the treatment of Goodpasture's syndrome (Bandarenko (1996) *Clinics in Laboratory Medicine* 16:907–929); and the treatment of cisplatin and mitomycin C-induced hemolytic uremic syndrome/ thrombotic thrombocytopenia purpura (HUS/TTP) (Watson et al. (1989) *Cancer* 64:1400; Snyder et al. (1993) *Cancer* 71:1882–1892).

The use and efficacy of viral immunogenic therapeutic agents that promote target specific treatment can be limited by the body's own immune system. The current invention addresses this limitation by providing methods to enhance performance of therapeutic viral vectors by partially pre-empting the body's immune defenses.

All publications cited herein are hereby incorporated by reference in their entirety.

DISCLOSURE OF THE INVENTION

The present invention provides methods and compositions for reducing pre-existing humoral immunity to immunogenic viral therapeutic agents.

Accordingly, in one aspect, the invention provides methods of reducing pre-existing humoral immunity to a viral immunogenic therapeutic agent in an individual comprising treating (i.e., contacting) the individual's blood extracorporeally with an immunosorbent that selectively binds anti-virus antibody to the viral therapeutic agent; removing antibody-immunosorbent complexes formed during the treatment, if any; and returning the blood to the individual. The viral immunogenic therapeutic agent may be any of a number of viruses such as adenovirus. The immunosorbents may be any of a number of substances which specifically bind to the antibody, such as organic molecules and polypeptides. Viral surface proteins are preferred.

In another aspect, the invention provides methods of reducing pre-existing humoral immunity to a viral immunogenic therapeutic agent in an individual comprising selectively removing antibody which specifically binds to the viral immunogenic agent from blood of the individual, wherein the antibody is selectively removed by extracorporeally binding the antibody to an immunosorbent which specifically binds to the antibody; removing immunosorbent-antibody complexes, if any; and returning the blood to the individual.

In another aspect, the invention provides methods of administering a viral therapeutic agent to an individual, comprising the steps of: (a) treating the individual's blood extracorporeally with an immunosorbent that binds antibody; (b) removing antibody-immunosorbent complexes formed during the treatment, if any, from the blood; (c) returning the blood to the individual; and (d) administering the viral therapeutic agent to the individual.

In another aspect, the invention provides kits for use in conjunction with these methods (i.e., for selective removal and/or detection of anti-virus antibody) comprising an immunosorbent that specifically binds the antibody to be removed in suitable packaging.

In another aspect, the invention provides compositions for selectively removing antibody which specifically binds to a viral immunogenic agent from blood of the individual, comprising an immunosorbent which specifically binds to the antibody conjugated to a matrix.

MODES FOR CARRYING OUT THE INVENTION

Figure 1:
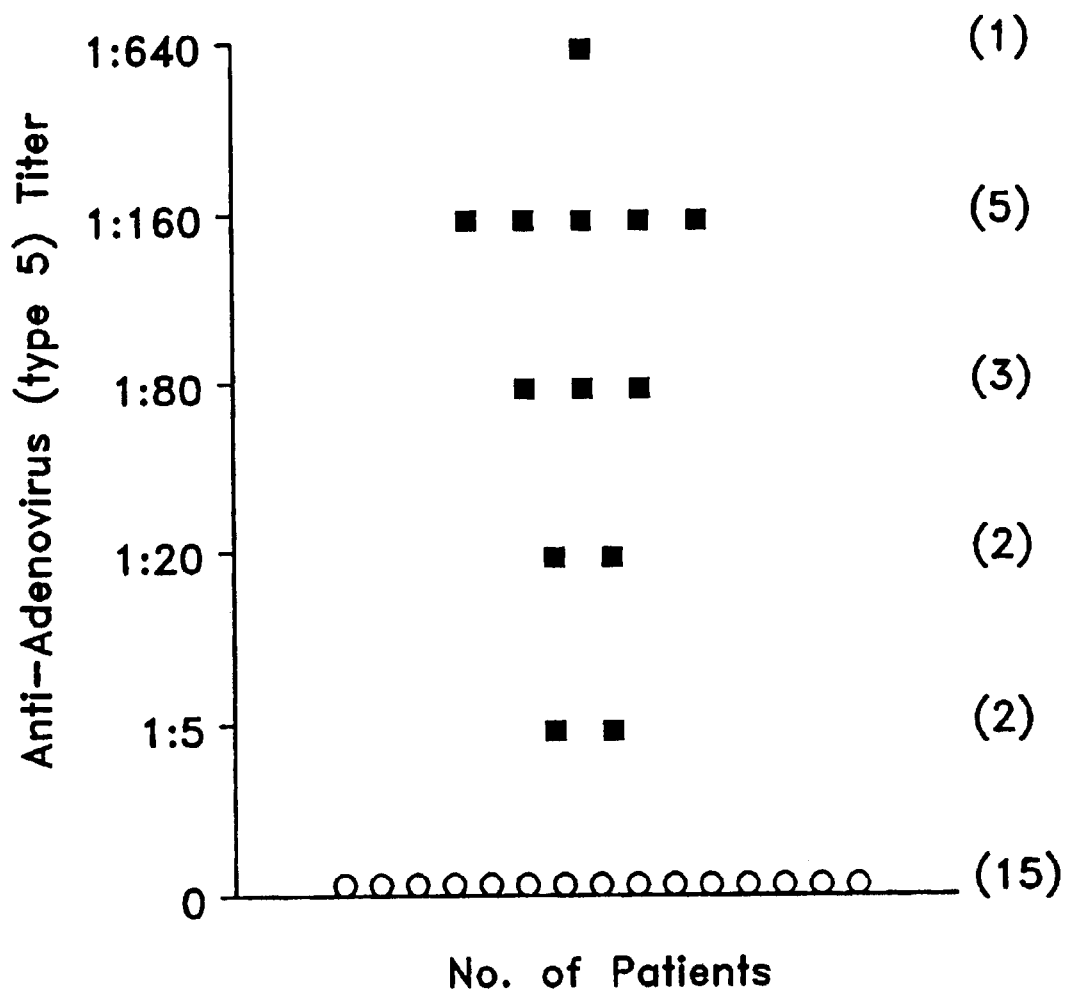
FIG. 1 is a graph depicting the prevalence of anti-adenovirus antibody (adenovirus serotype 5) in prostate cancer patients. The graph shows that anti-virus antibodies were found in 13 of the 28 samples (46%) with titers ranging from 1:5 (n=5) to 1:640 (n=1).

We have discovered methods and compositions useful for reducing pre-existing humoral immunity to a viral immunogenic agent, particularly a viral therapeutic agent, in an individual. By removing antibodies to the viral immunogenic agent in an individual's blood before its administration as a therapeutic agent, the individual's pre-immunity to the viral immunogenic agent is reduced.

We have found and believe that by removing antibodies specific to the viral therapeutic agent, the effectiveness of the treatment is increased. Upon administration of the viral therapeutic agent once the antibodies that specifically bind to the viral therapeutic agent have been selectively removed from the individual, there should be a prolonged presence of the therapeutic agent in the blood and increased dissemination. This prolonged presence (i.e., increased half life) should increase the effectiveness of the viral agents. For example, an agent should then be able to more effectively reach metastatic sites. Without wishing to be bound by any particular theory, pre-existing humoral immunity is decreased due to removal of antibody, thereby delaying immuno-destruction of the viral therapeutic agent, thus allowing it more effective dissemination and a longer half-life.

General Techniques

The practice of the present invention will employ, unless otherwise indicated, conventional techniques of cell biology, immunology, molecular biology, biochemistry, and adenovirus biology, all of which are within the skill of the art. Such techniques are explained fully in the literature, such as, "Antibodies: A Laboratory Manual," (Harlow, E. and Lane, D., 1988); "Physical Biochemistry: Applications to Biochemistry and Molecular Biology," second edition (Freifelder, D., 1982); "Handbook of Experimental Immunology," (D. M. Wei & C. C. Blackwell, eds); "Gene Transfer Vectors for Mammalian Cells," (J. M. Miller and M. P. Calos, eds. 1987); "Current Protocols in Immunology," (J. E. Coligan et al., eds., 1991); Felgner and Ringold (1989) *Nature* 337:387–388; Berkner and Sharp (1983) *Nucl. Acids Res.* 11:6003–6020; Graham (1984) *EMBO J.* 3:2917–2922; Bett et al. (1993) *J. Virology* 67:5911–5921; Bett et al. (1994) *Proc. Natl. Acad. Sci. USA* 91:8802–8806.

Definitions

An "antibody" (interchangeably used in plural form) is an immunoglobulin molecule capable of specific binding to a target, such as a polypeptide, through at least one antigen recognition site, located in the variable region of the immunoglobulin molecule. An antibody can be from any source of animal capable of producing them, for example, mouse, rat, rabbit, or human antibodies. As used herein, the term encompasses not only intact antibodies, but also fragments thereof (such as Fab, Fab', F(ab')$_2$, Fv, single chain (ScFv)), mutants thereof, fusion proteins, humanized antibodies, and any other modified configuration of the immunoglobulin molecule that comprises an antigen recognition site of the required specificity. The term "antibody" includes polyclonal antibodies and monoclonal antibodies. An "anti-idiotype" antibody refers to a type of antibody which mimics the structure of an antigen to which another antibody is specific.

The term "antigen" as used herein is any substance that reacts in a demonstrable way with antibodies and/or immune cells. An antigen contains a determinant group within the molecule for the particular chemical group of another molecule that confers antigenic specificity.

The term "blood" as used herein is bodily fluid including a cellular component and plasma. "Blood" means whole blood or a component thereof. Treating an "individual's blood" means that any or all of an individual's blood is treated.

The term "immunosorbent" as used herein refers to a molecule containing an epitope specific to antibodies against a immunogenic viral therapeutic agent, i.e., a molecule which specifically binds to an anti-viral agent antibody. The term "epitope" as used herein refers to any form of an antigenic determinant.

The terms "immunogenic viral therapeutic agent," "viral therapeutic agent," and "viral agent" are used interchangeably and refer to a virus or viral construct (i.e., derived from a viral genome) administered to an individual to treat an abnormal condition or disease state, which, when introduced into an individual, elicits circulating antibodies specific for that viral agent. Examples of viral therapeutic agents are described herein.

The term "individual" as used herein is a vertebrate, preferably a mammal, more preferably a human. Mammals include, but are not limited to, farm animals, sport animals, pets, mice, monkeys, chimpanzees and other laboratory animals.

The term "anti-virus antibody" as used herein refers to an antibody specific for a viral therapeutic agent. An "anti-virus antibody" includes, but is not limited to, a neutralizing antibody specific for a viral therapeutic agent. It is understood that occasional use of the term "neutralizing antibody" in the specification (including the Examples section and accompanying figures) does not indicate that the invention is limited to so-called "neutralizing" antibodies.

The term "pre-existing humoral immunity" as used herein refers to the presence of antibodies which specifically bind to a viral therapeutic agent in an individual. For purposes of this invention, these antibodies have been elicited due to prior exposure to an immunogenic viral agent, whether or not in the same form as the agent actually used for therapy (for example, an individual may have pre-existing immunity to an adenoviral agent due to exposure to wild type adenovirus), and/or whether before or during the course of therapy with the agent.

The term "selective removal" refers to a reduction in antibody amount, or titer, preferably at least about 50%, preferably at least about 60%, preferably at least about 80%, preferably at least about 85%, preferably at least about 90%, preferably at least about 95%. Methods of measuring antibody titer, either by binding or neutralizing assays, are well known in the art.

A "stable complex" is one that sufficiently persists after its formation to allow subsequent detection and/or removal.

A "trimeric" protein or a "trimer" as used herein refers to a multimeric protein containing three separate polypeptides or protein chains associated with each other in vitro or in vivo. The association may be covalent and/or non-covalent. The trimeric protein may consist of three polypeptide chains of the same sequence. A multimeric protein may also be composed of more than one polypeptides having distinct sequences to form, e.g., a heterdimer or a heterotrimer.

Methods of the Invention

The invention provides methods of reducing pre-existing humoral immunity to a viral immunogenic therapeutic agent by selectively removing anti-virus antibodies to the viral immunogenic therapeutic agent. Generally, the anti-virus antibody is selectively removed by: (a) treating or contacting the individual's blood (i.e., all or portion thereof) extracorporeally with an immunosorbent that selectively binds the anti-virus antibody; (b) removing the antibody-immunosorbent complexes from the blood formed during the treatment, if any; (c) and returning the blood to the individual. Stated alternatively, antibody which specifically binds to the viral immunogenic agent is selectively removed from blood of an individual, wherein this removal is accomplished by extracorporeally binding the antibody to an immunosorbent which specifically binds to the antibody and removing immunosorbent-antibody complexes formed, if any. The blood is then returned to the individual. If cellular components have been separated from plasma (or serum), plasma and cellular components are reintegrated before infusing the individual with the blood. The viral therapeutic agent is then administered to the individual, who has reduced pre-existing humoral immunity to the viral agent. Examples of a viral therapeutic agent include (and/or may be derived from), but not limited to, adenovirus, Moloney mouse leukemia virus (MoMLV), herpes virus, pox virus, adeno-associated virus (AAV), and HIV.

Initially, a sample of blood is usually taken in order to determine the anti-virus antibody titer and thus determine whether selective removal of antibody is warranted, and this measurement and determination is an optional step in the methods described herein. For purposes of this invention, antibody measurements may be made using standard techniques in the art, such as RIA and neutralizing assays. In a neutralizing assay, mammalian cells (such as 293 cells) are infected with a known multiplicity of infection (MOI) of the virus which has been pre-incubated in a known dilution of serum (antibody). Control virus is not pre-incubated. See, for example, Gahery-Segard et al. (1997) *Eur. J. Immunol.* 27:653–659. Cytophathic effect (CPE) is measured and compared to control virus. Dilutions are generally reported for the dilution that achieves 100% protection (i.e., no cytopathic effect). An example of a protocol for an in vitro neutralizing assay which can be used for adenovirus is as follows. Human 293 cells are pre-seeded in 96-well plates at $1\times10^4$ cells per well and cultured at 37° C., 5% $CO_2$ overnight. Serum or plasma samples are incubated at 56° C. for 20 minutes to inactivate the complement system, followed by addition of 50 µl complete RPMI into the plates. Fifty µl of undiluted test samples are added to each well at serial dilutions to a different plate. Adenovirus is diluted in complete RPMI to $2\times10^5$ pfu/ml, and 50 µl diluted virus is added to the wells, followed by incubation at 37° C. for one hour. The mixtures (control and samples with virus) are then removed from the wells and added to the plate containing the 293 cells and incubated for one hour at 37° C. After removing the mixtures from the plate, 100 µl of fresh media are added to each well, followed by incubation at 37° C. and 5% $CO_2$ (observed daily). The control well would be expected to undergo 100% CPE after approximately 5 to 7 days, at which point test wells are checked for CPE (in 293 cells). The titer of neutralizing antibody is expressed as the inverse of the lowest dilution required to produce 100% inhibition of CPE.

In the case of adenovirus, cells are infected with MOI of 1, and selective removal of the anti-virus antibody is recommended for efficacious treatment with the therapeutic viral agent if the titer is greater than about 1:10, more preferably more than about 1:20. In terms of total anti-adenovirus antibody individuals indicated for the apheresis procedure have a total anti-adenovirus antibody above about any of the following: 12 µg/ml, 15 µg/ml; 20 µg/ml; 25 µg/ml; 30 µg/ml; 50 µg/ml; 60 µg/ml; 75 µg/ml. Total anti-adenovirus antibody may be determined using methods known in the art, such as ELISA. Molnar-Kinber et al. (1998) *Human Gene Ther.* 9:2121–2133.

Binding an Immunosorbent to Anti-Virus Antibody

In the methods of the invention, blood is removed from the individual for extracorporeal binding to an immunosorbent. Apparatuses and methods for removing blood and separating it into its constituent components are known in the art (see, e.g., U.S. Pat. Nos. 4,086,924; 4,223,672). The blood or portions thereof are then exposed to an immunosorbent capable of specifically binding anti-virus antibodies. This binding interaction between the anti-virus antibody and the immunosorbent initiates the process of reducing pre-existing humoral immunity to the viral therapeutic agent.

The immunosorbent may be any chemical moiety (whether biochemical (such as polypeptide), organic or inorganic), as long as the molecule has the requisite specificity in binding activity with the anti-virus antibodies. The immunosorbent may include, but is not limited to, any of the following: antigenic portions of the viral vector (including the virus itself), a protein or other molecular structure containing an epitope specific to anti-viral vector antibody, anti-idiotype antibodies specific for the anti-viral vector antibody, and F'ab fragments of the aforementioned antibodies. It is understood that, for purposes of this invention, one or more immunosorbents may be used, i.e., a combination of different immunosorbents and/or a single immunosorbent. Immunosorbents may be made using standard techniques in the art, such as chemical synthesis and recombinant techniques.

Generally, surface proteins and proteins that encapsulate the virion's genetic material are suitable for use in the preparation of immunosorbents described in the methods of the invention. Anti-virus antibody specific for the various viruses predominantly appear to be specific for either surface envelope proteins or capsid proteins. It is also these proteins that distinguish one serotype of a virus from another. Intact (whole) viral polypeptides, fragments thereof, and fusion polypeptides containing at least an immunoreactive portion of a viral polypeptide may be used, as long as specific binding activity is present. Testing specific binding can be readily accomplished using standard binding assays in the art, such as ELISA or immunoprecipitation. Of the above-mentioned therapeutic viruses, adenovirus, herpes simplex virus, AAV and HIV have well characterized surface and encapsulation proteins that may be suitable candidates as immunosorbents.

Figure 13A:
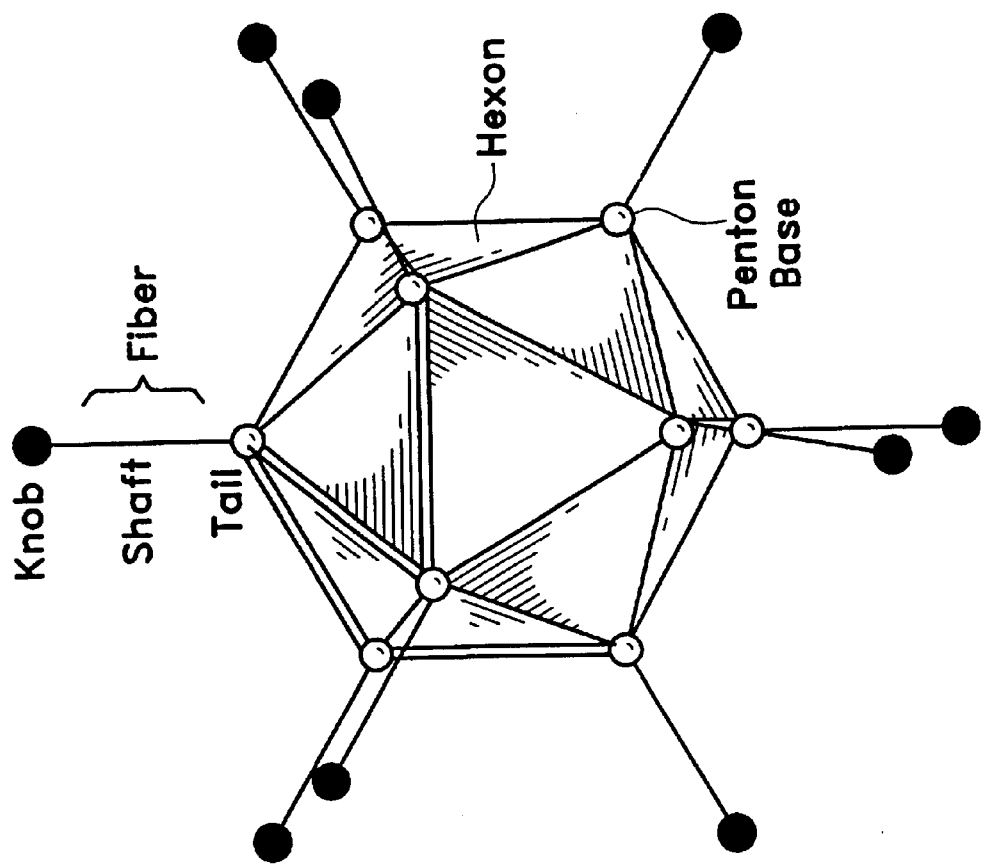
FIG. 13(A) is a schematic representation of an adenovirus particle.
Figure 13B:
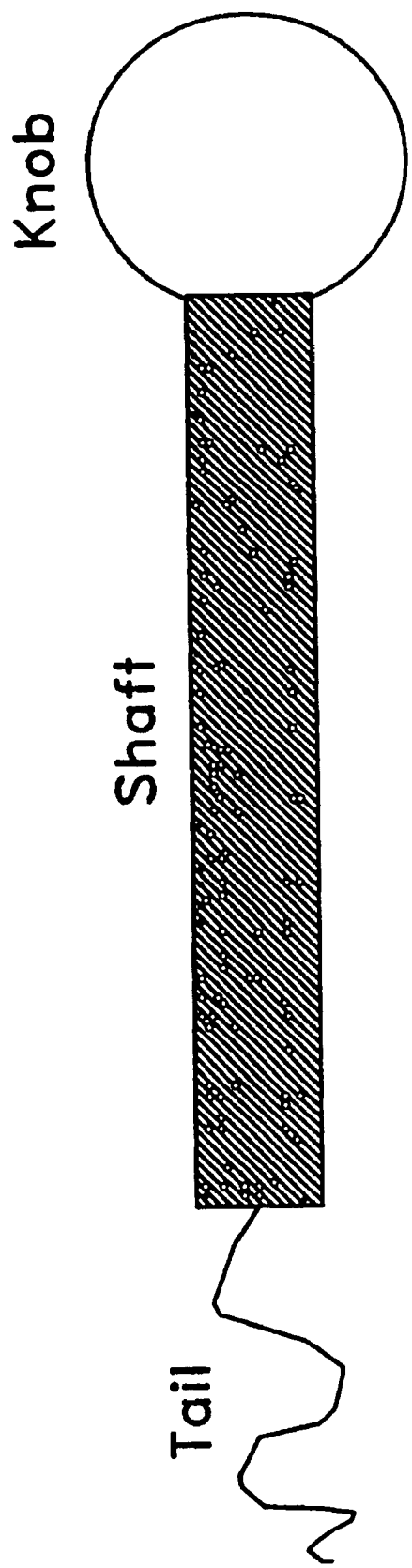
FIG. 13(B) is a schematic representation of the structure of a monomeric adenovirus fiber protein.
Figure 14:
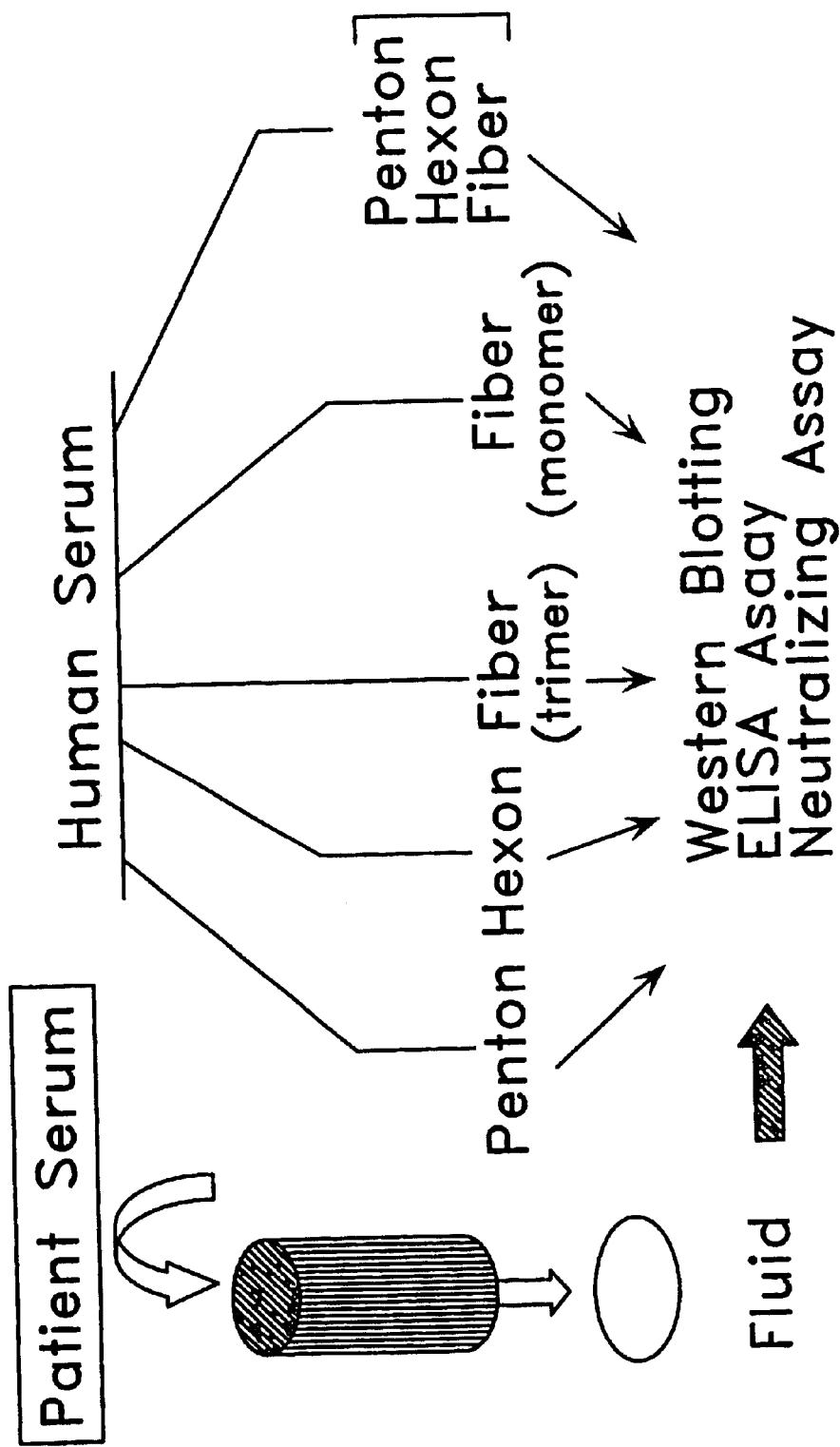
FIG. 14 is a diagram depicting the application of various affinity columns for adenovirus, each containing penton, timeric fiber, monomeric fiber, hexon proteins alone, or a mixture of penton, hexon and fiber proteins.

With respect to adenovirus, candidate polypeptides which would specifically bind to an anti-adenovirus neutralizing antibody are surface proteins. Schematically, FIG. 13 depicts these proteins. Non-enveloped adenoviral particles contain at least 11 different proteins (Maizel et al. (1968) *Virology* 36:115–125), but are composed primarily of hexon and penton capsomers. Fiber protein projects from the virion surface and makes the primary contacts with the cellular receptor, and variations in fiber protein sequence contribute to the tissue tropism of different adenovirus isolates. Arnberg et al. (1997) *Virology* 227:39–244. Neutralizing antibodies react to the type-specific antigenic determinants on the hexon and fiber polypeptides. Sequences of these adenovirus surface proteins are known in the art. See, e.g., Reubel et al (1997) *Arch. Virol.* 142(6): 1193–212; Pring-Akerblom et al. (1995) *Res. Virol.* 146(6):383–388; Weber et al. (1994) *J. Gen. Virol.* 75:141–147. Preferably, the immunosorbent is an adenovirus surface protein, a fragment thereof, or a fusion polypeptide thereof that retains binding specificity to an anti-adenovirus antibody. More preferably, the surface protein is selected from the group consisting of adenovirus hexon protein, fiber protein, penton protein, and any combination thereof. Accordingly, the adenovirus surface protein used as an immunosorbent may be any of the following: hexon protein; fiber protein; penton protein; hexon protein and fiber protein; hexon protein and penton protein; fiber protein and penton protein; hexon protein, fiber protein, and penton protein. A particularly effective immunosorbent is a combination of hexon, fiber and penton protein, or a fiber protein assembled in a trimeric conformation. The combination may be effected sequentially or concurrently (i.e., the combination may occur due to, for example, conducting separate reactions or, alternatively, may be effected by combining all three proteins (for instance, on a single column) as a mixture). We observed that *E. coli* expressed fiber proteins are capable of reassembling into trimeric proteins, generally under phydiological conditions (such as use of suitable buffers and without detergent). FIG. 14 schematically depicts these various column configurations.

Neutralizing antibodies for herpes simplex viruses have been found for envelope proteins, such as glycoproteins. The majority of neutralizing antibodies for herpes simplex virus type 1 are specific for glycoproteins B, C and E. Eing et al. (1989) *J. Med. Virol.* 27(l):59–65. Glycoprotein D has been shown to be a major target antigen for neutralizing antibody. Highlander et al. (1987) *J. Virol.* 61(11)3356–64. Glycoproteins A, B and D of herpes simplex virus type-common act as targets for neutralizing antibodies and thus would be good candidates for use in the preparation of immunosorbents. Vestergaard (1980) *Rev. Infect. Dis.* 2(6):899–913; Browne et al. (1993) *J. Gen. Virol* 74:2813–2817; Sanchez-Pescador et al. (1993) 168(4):844–853; Cohen et al. (1992) *Adv. Exp. Med. Biol.* 327:217–228.

The antigenicity of the various adeno-associated viruses (AAV) types appears to derive from the differences in their capsid proteins, and thus capsid proteins would be good candidates for binding to neutralizing antibodies (FIG. 13(*a*)). Sixty percent of an adult test population had antibodies to structural components to AAV type 5. George-Fries et al. (1984) *Virology* 134(1):64–71. In describing a new serotype of AAV (type 6), Rutledge et al. (1998) found significant sequence variation in portions of capsid proteins that are thought to be responsible for serotype specific functions, such as resistance to neutralizing antibodies against type 2. *J. Virol.* 72(1):309–19.

HIV's surface proteins (Env), which have high variability, are the predominant target of neutralizing antibodies. Durali et al. (1998) *J. Virol.* 72(5):3547–53. Among different cladi of HIV some epitopes appear to be conserved, namely, Gag p24, Gag p18, integrase and the central region of Nef. Neutralizing epitopes have also been found in the V3 loop and the CD4-binding domain of gp120, as well as near the transmembrane region of gp41. Hioe et al. (1997) *Int. Immunol.* 9(9):1281–90. If HIV is to be used as a viral vector, these various epitopes may be used in immunoapheresis as immunosorbents to temporarily reduce neutralizing antibodies to HIV.

In addition to viruses and their various components, other candidates as immunosorbents are anti-idiotype antibodies. Anti-idiotype antibodies mimic the structure of an antigen in their hypervariable regions. Anti-idiotype antibodies may be raised by using known anti-virus antibodies. An example of developing such antibodies is as follows: (1) inject a mouse with the viral vector to induce production of anti-virus antibodies; (2) harvest B cells from the mouse using primary culture and fuse the cells with a myeloma cell line to make a hybridoma; (3) screen the hybridomas for production of anti-virus antibody by using an ELISA system with the viral vector as a substrate; (4) grow up the clones that are positive for anti-virus activity and purify the antibodies; (5) inject the anti-virus antibodies in a viral vector naive mouse to raise an immune response to the anti-virus antibodies thereby making the anti-idiotype antibodies; (6) harvest B cells from the viral vector naive mouse to make hybridomas; (7) screen the hybridomas for production of anti-idiotype antibodies and specific binding to anti-virus antibodies; (8) grow up large amounts of the anti-idiotype antibody for use as an immunosorbent. These antibodies may be used whole or in part as long as the fragments contain the region with the requisite specific binding activity.

Binding of anti-virus antibody to immunosorbent is allowed to occur by incubating blood (or blood component) with immunosorbent under conditions (easily empirically determined) that allow formation of an immunosorbent antibody complex stable enough to allow its removal.

Removing Immunosorbent-Antibody Complex

Once a stable complex is formed, two general methods may be used for removing these immunosorbent-antibody complexes from the blood or plasma. One utilizes a solid phase system (i.e., using a matrix bound to an immunosorbent) and another utilizes a liquid phase system. In a solid phase system, the immunosorbent specific to the anti-viral agent anti-virus antibody is attached to a solid phase matrix (i.e., a solid phase support to which the immunosorbent is bound). The blood or plasma (or serum) containing the antibody to be removed is passed over a solid phase support. The blood, plasma or serum exits the solid phase support leaving behind the immunosorbent-anti-virus antibody complex, thereby removing it from the blood. In a liquid phase system the immunosorbent-antibody complex is immunoprecipitated from the blood or plasma.

For the solid phase systems, any of a number of solid phase matrices may be used. Several commercially available matrices include, but are not limited to agarose (i.e., a neutral linear polysaccharide generally composed of D-galactose and altered 3,6-anhydrogalactose residues) such as Sepharose (Pharmacia), activated gels, nitrocellulose, borosilicate, glass fiber filters, silica, polyvinylchloride, polystyrene, and diazotized paper. The term "agarose" as used herein encompasses which is commonly used in chromatography.

Immunosorbent(s) is bound (i.e., conjugated) to the matrix, either covalently or non-covalently, before passing the blood or plasma (or serum) over the matrix. Matrices that may be non-covalently bound by incubation with the immunosorbent, usually at a temperature warmer than room temperature, include, but are not limited to, nitrocellulose, borosilicate, filters, polyvinylchloride, polystyrene and diazotized paper. Other matrices require a chemical reaction to covalently bind the immunosorbent to the matrix. Production of these activated matrices are well known in the art. See, e.g., U.S. Pat. No. 4,762,787. Some are commercially available, such as epoxy-activated agarose, requiring only incubation with the activated matrix. Others include, but are not limited to, CNBr-activated agarose, 6-aminohexanoic-acid and 1,6-diaminohexane-agarose, epoxy-activated agarose, thiopropyl agarose, carbonyldiimidazole-activated agarose, aminoethyl and hydrazide activated polyacrylamide. See, e.g., "Physical Biochemistry: Applications to Biochemistry and Molecular Biology," second edition (Freifelder, D., 1982).

In embodiments in which a polypeptide immunosorbent is bound to a support matrix, the molecular weight of the polypeptide immunosorbent is preferably less than about 150 kD, preferably less than about 125 kD, preferably less than about 100 kD, preferably less than about 90 kD, preferably less than about 75 kD, preferably less than about 60 kD, preferably less than about 50 kD. Smaller molecular weights lessen any negative effects due to steric hindrance.

In other embodiments of the invention, an affinity column is used, in which a solid phase matrix bound to an immunosorbent is contained in a cylindrical container with filters on both ends to prevent particulate matter from entering or leaving the column. For these embodiments, the blood of the individual is separated into its plasma and cellular components because whole blood contains cells and particulate matter (such as platelets) which can impede the flow through a column. Plasma may be further processed into serum by removing clotting proteins, which would also improve flow efficiency through a column. The plasma or serum is passed over the column(s) and the plasma or serum is collected leaving the immunosorbent-antibody complex behind in the column.

Another solid phase embodiment includes nitrocellulose sheets preincubated with an immunosorbent. Blood, preferably plasma or serum, is collected from the individual, incubated with the immunosorbent-linked nitrocellulose, and then collected leaving the immunosorbent-antibody complex attached to the nitrocellulose.

Another solid phase technique that may be used is commonly known in the art as "panning". Large polystyrene petri dishes are incubated with immunosorbent until bound to its surface. Blood, plasma or serum from the individual is incubated with the immunosorbent-linked polystyrene and is decanted. The anti-viral vector antibody remains behind linked to the immunosorbent which is linked to the polystyrene.

In some embodiments, pre-clearance of antibody, or a class of antibodies, such as IgG or IgA, is performed before selective removal of anti-virus antibody. The specific anti-virus antibody may then be extracted from the larger pool of antibody. The remaining antibody is reconstituted into the blood to be reperfused into the individual. These methods decrease the volume that must be passed over the immunosorbent specific for the antibody of interest in addition to decreasing non-specific binding that may occur with other moieties in the plasma. For example, nonspecific Protein A or Protein G Sepharose columns, such as PROSORBA® (IMRE, Munich, Germany), may be used to remove a significant portion of IgG antibody with some removal of the other classes of antibody from plasma. This antibody can then be eluted and purified according the protocols known in the art, as those in "Antibodies: A Laboratory Manual," (Harlow, E. and Lane, D., 1988). The purified antibody may then be passed over an a solid phase matrix linked with an immunosorbent specific for the viral vector, preferably an adenoviral vector, thereby separating the anti-virus antibody from other types of antibody. The eluent may then be reconstituted into the plasma to be mixed with cellular components to be reintroduced to the individual with the anti-virus antibody having been removed.

General pre-clearance (i.e., isolation) of antibody may also be accomplished using ammonium sulfate precipitation with ion exchange chromatography, caprylic acid, DEAE-matrix (ion exchange chromatography), hydroxyapetite chromatography, or gel filtration (Sepharose). These techniques are well known in the art. Harlow, E. and Lane, D., 1988. Once antibody has been isolated and solubilized, it may be exposed to the immunosorbent linked to a matrix as described above. The resulting eluent may then be processed for reintroduction to the individual.

In some embodiments of the invention, methods of administration of a viral therapeutic agent are provided, wherein an individual's blood is treated extracorporeally with an immunosorbent that binds antibody, the antibody-immunosorbent complexes formed during the treatment (if any) are removed, the blood is returned to the individual, and viral therapeutic agent is administered to the individual. The immunosorbent may be any material (as described above) that reacts with any antibody (including types, or class, of antibody), such as protein A or protein G. Similarly, the antibody removed in these methods may be any, or all, types or classes. Preferably, the viral therapeutic agent is adenovirus.

In another embodiment of the invention, an immunosorbent specific for anti-virus antibodies is bound to lipid vesicles. These lipid vesicle-immunosorbents are then mixed with an individual's plasma or serum to allow binding, and the plasma or serum is then filtered to remove the lipid vesicle-immunosorbent-antibody complex. U.S. Pat. No. 4,643,718.

In other embodiments, immunosorbent-antibody complex is removed using a liquid (as opposed to solid) phase. For example, an immunosorbent is conjugated to a hapten. The hapten can be, but is not limited to, dinitrophenol or fluorescein. The hapten-immunosorbent complex is mixed with the individual's blood, preferably plasma or serum. The hapten-immunosorbent complex binds to the anti-virus antibody. Immune complexes are formed with the introduction of anti-hapten antibodies which bind to the hapten-immunosorbent-antibody complex. These complexes are precipitated using, for example, polyethylene glycol (PEG) which may be separated from the plasma or serum using centrifugation. See, e.g., U.S. Pat. No. 4,551,435. Treatment of plasma or serum to remove residual polyethylene glycol prior to reintroduction into the individual is known in the art.

The titer of the anti-virus antibody is usually determined after selective removal in order to assess whether sufficient antibody has been removed, and this determination is an optional step in the methods described herein. Generally, sufficient removal to reduce the effect of a humoral immune response on viral efficacy, while maintaining sufficient antibody so that recovery (i.e., production) will permit later protection against viral infection, is preferred. Complete removal of anti-virus antibody is not necessary or even necessarily preferred. Based on a neutralizing assay (described above), the titer after selective removal of anti-adenovirus antibody is not less than about (i.e., at least about) 1:50, preferably not less than about 1:20, preferably not less than about 1:15, preferably not less than about 1:10, more preferably not less than about 1:5, even more preferably not less than about 1:1. The degree and extent of removal that is required to be efficacious can be readily determined empirically, and may vary depending on the particular disease state to be treated, the condition of the individual, the nature and type of the viral agent used (as well as the treatment protocol), and/or whether other therapeutic agents are used in conjunction with the viral agent(s).

Accordingly, in some embodiments, the invention provides methods of selective removal of anti-virus antibody, wherein titer of anti-virus antibody after treatment is not less than about 1:20, preferably not less than about 1:10. The invention also provides methods wherein the individual's titer of anti-virus antibody before treatment (i.e., before selective removal) is at least about 1:10 or at least about 1:20. In some embodiments, the viral therapeutic agent to be used is adenovirus. In some embodiments, the anti-virus antibody is adenovirus penton protein.

Returning the Blood to the Individual

Once anti-virus antibody-immunosorbent complex is selectively removed (or, in accordance with some embodiments, one antibody-immunosorbent complex is removed), the blood is reintroduced to the individual, or the plasma or serum is reintegrated with the cellular components of the blood to be returned to the individual (apheresis). The general methods of removal of the blood and its return to the individual are well known in the art and are described in the above listed patents and publications. Two processes commonly used are continuous and discontinuous processes. The continuous process involves removing the blood of an individual in a steady flow, separating the plasma from the cellular components, treating the plasma, recombining the plasma with the cellular component and then reinfusing the individual. The discontinuous process involves removing a small volume of blood, separating the plasma from the cellular components of that particular volume, treating the plasma of that volume, reconstituting the two components and reinfusing the volume into the individual.

Administration of the Therapeutic Viral Agent

After anti-virus antibody-immunosorbent complex has been selectively removed (or, in accordance with some embodiments, one antibody-immunosorbent complex is removed), a viral therapeutic agent may be administered in a variety of ways. The viral agent may be administered by adding it to the reintegrated blood to be reinfused into the individual. Alternatively, the viral agent may be administered via injection, such as intravenous, intramuscular, subcutaneous, and intratumoral injection. Other methods of administration may include peroral dosage, suppository, or inhalant. The method of administration would generally depend on the location of the target of the viral agent. For example, if the target were the lungs, an inhalant may be preferable over an intravenous injection. If the target was in the blood, or in multiple metastatic sites, an intravenous injection would be preferable.

Administration should occur before anti-virus antibody titer significantly increases. The rate at which this titer significantly increases depends upon any of several variables such as the condition of the individual and the viral agent to be used. Preferably, viral therapeutic agent is administered within a week of selective removal of anti-virus antibody, more preferably within three days of selective removal of anti-virus antibody, more preferably within two days of selective removal, more preferably within one day of selective removal, more preferably within 24 hours of selective removal, more preferably within 12 hours of selective removal, even more preferably within 6 hours of selective removal, even more preferably within 3 hours of selective removal.

Generally, selective removal may be effective for up to one to two weeks, while a therapeutic virus (such as adenovirus) may need to be present in circulation for three to four weeks or more to be efficacious. Thus, after treatment with the therapeutic viral agent, anti-virus antibody titer is optionally monitored, generally at regular time points (such as once a week). In the case of adenovirus, and as measured in the neutralizing assay described above, titers above about 1:10, preferably above about 1:20 may indicate another treatment to selectively reduce anti-virus antibody in order to maintain therapeutic levels of the viral agent.

The amount (i.e., dosage) of viral therapeutic agent to be administered will depend on a variety of factors, including, but not limited to, the disease to be treated, the condition of the individual, and/or the extent of the reduction of humoral immunity. Generally, the greater the extent of reduction of anti-virus antibody, the more dosage may be reduced. Care must be taken to administer an efficacious amount of the virus without incurring unacceptable side effects (due to administered virus to a partially immunocompromised individual). Preferably, a residual titer of circulating antibody is present.

In cases in which an individual is significantly or severely immunosuppressed, re-infusion of anti-virus antibody may be advisable after a sufficient time after treatment with a viral therapeutic agent. A "sufficient time" in this context means that the viral therapeutic agent is allowed to be effective, which may vary depending on the viral agent used, the condition of the individual, the dosage, and/or the disease to be treated. For example, in the case of adenovirus, a period of two to three weeks should be allowed before administering anti-virus antibody.

Combination Therapy with Immunosuppressants and/or Cytokines

The methods described herein may be used in conjunction with other agents or methods that effect immunosuppression. Prior to, or concurrently with, the administration of the viral immunogenic therapeutic agent, immunosuppressants, cytokines, or monoclonal antibodies that block either the T cell receptor or costimulation pathways necessary for T cell activation may be administered. In addition to the decrease in humoral immunity effected by selective removal of anti-virus antibodies, prior administration of immunosuppressants, cytokines or monoclonal antibodies may pre-empt a cellular response that would occur upon administration of the viral agent. Cytokines such as interleukin-12 (IL-1 2) and interferon (IFN) block production of IgA antibodies by B cells. The use of these cytokines are particularly important if the administration of the vector is via the lungs because the body's normal response to viral invasion via the lungs include increases in IgA as a anti-virus antibody. U.S. Pat. No. 5,652,224. Immunosuppressants include, but are not limited to, Cyclosporine A (CsA) (Sandoz Pharmaceuticals Corp., N.J.) which blocks recruitment of CD8+ T cells, FK506 which prevents T cell differentiation and proliferation; Deoxyspergualin (DSG) (Nippon Kayaku Co., Ltd., Japan) which prevents production of antibody by B cells; and cyclophosphamide (CyP) which prevents production of antibody. Monoclonal antibodies that are specific to the T cell receptor and costimulatory pathways and have prolonged transgene expression with adenoviral vectors by decreasing anti-virus antibody production are described in: Christ et al. (1997) *Immunology Letters* 57:19–25; Sawchuck et al. (1996) *Hum. Gene Ther.* 7:499–506; Guerette et al. (1996) *Hum. Gene Ther.* 7:1455–1463; Kay et al. (1995) *Nature Genet.* 11:191–197. The use of immunosuppressants and/or cytokines and/or monoclonal antibodies specific for T cell receptors or costimulatory pathways in conjunction with immunoapheresis decreases the body's immune response to the administration of the viral immunogenic therapeutic agent.

Kits and Compositions of the Invention

The invention also includes kits and compositions for use in conjunction with the methods described herein. In some embodiments, the kits and compositions effect extracorporeal selective formation and/or removal of immunosorbent-anti-viral antibody complexes. These kits and compositions contain components specific for antibodies against viral therapeutic agents, aiding their extracorporeal removal from blood order to reduce the pre-existing humoral immunity to the therapeutic agent. In other embodiments, kits and compositions are provided for use in detection of anti-viral antibodies. These kits and compositions aid in assessing (a) whether an individual is indicated for selective removal of anti-viral antibody (for example, if the titer is considered to be above a requisite threshold); (b) monitoring an individual after treatment (i.e., selective removal) to determine whether further sufficient removal has occurred and/or whether further is indicated (for example, when a period of time has elapsed since removal, and the titer of anti-viral antibody has risen to or past a requisite threshold, and treatment with a viral therapeutic agent is still indicated); (c) which anti-viral antibody(ies) an individual is producing (this would indicate which antibody or antibodies should be selectively removed). These kits and compositions contain components specific for antibodies against viral therapeutic agents, aiding detection and/or monitoring.

It is understood that these kits, especially those used to effect selective removal of anti-virus antibody, may also be, and can be denoted, "systems".

Kits of the invention comprise an immunosorbent that specifically binds the anti-virus antibody to be removed in suitable packaging. Preferably, the kit also contains instructions for its use. Immunosorbents have been discussed above. The kits may include one or more such immunosorbents. In addition, the kit may include a separation device (i.e., one or more separation devices). An example of a separation device that may be included in the kit is a pre-packed chromatography column pre-linked to an immunosorbent adaptable for an apheresis device. Another example of a separation device is a pre-packed column without pre-linkage to an immunosorbent. In such a kit, a choice of immunosorbents may be provided, allowing the user to define the specificity of the column. Other separation devices include, but are not limited to, other solid phase supports as previously described such as nitrocellulose, polystyrene, and glass fiber filter.

The kits of the invention may or may not include a matrix which is pre-bound to the immunosorbent(s). In the instance the immunosorbent is not pre-bound to a matrix, the kit may also optionally include pre-measured buffers for activation of the matrix and coupling the immunosorbent to the matrix. The pre-measured buffers may be available in fully constituted forms ready for use, or may constitute pre-measured materials requiring appropriate dilution. In some embodiments, an immunosorbent is an adenovirus penton protein. One or more immunosorbents may be present in the kit.

The kits of the invention may further comprise an immunogenic viral therapeutic agent to be administered to the individual. In such a kit, the matching immunosorbents to the viral agent would be provided. The kits may also contain reagents for testing for the presence (and/or level) of anti-virus antibody, which would be useful for monitoring purposes.

The invention also provides compositions for selectively removing antibody which specifically binds to a viral immunogenic agent from blood of the individual, comprising an immunosorbent which specifically binds to the antibody conjugated to a matrix. Matrices have been discussed above. Another composition of the invention is one in which the immunosorbent is conjugated to a hapten.

The following examples are provided to illustrate but not limit the invention.

EXAMPLES

Example 1

Effect of Pre-existing Humoral Immunity on Adenoviral Efficacy

Figure 3:
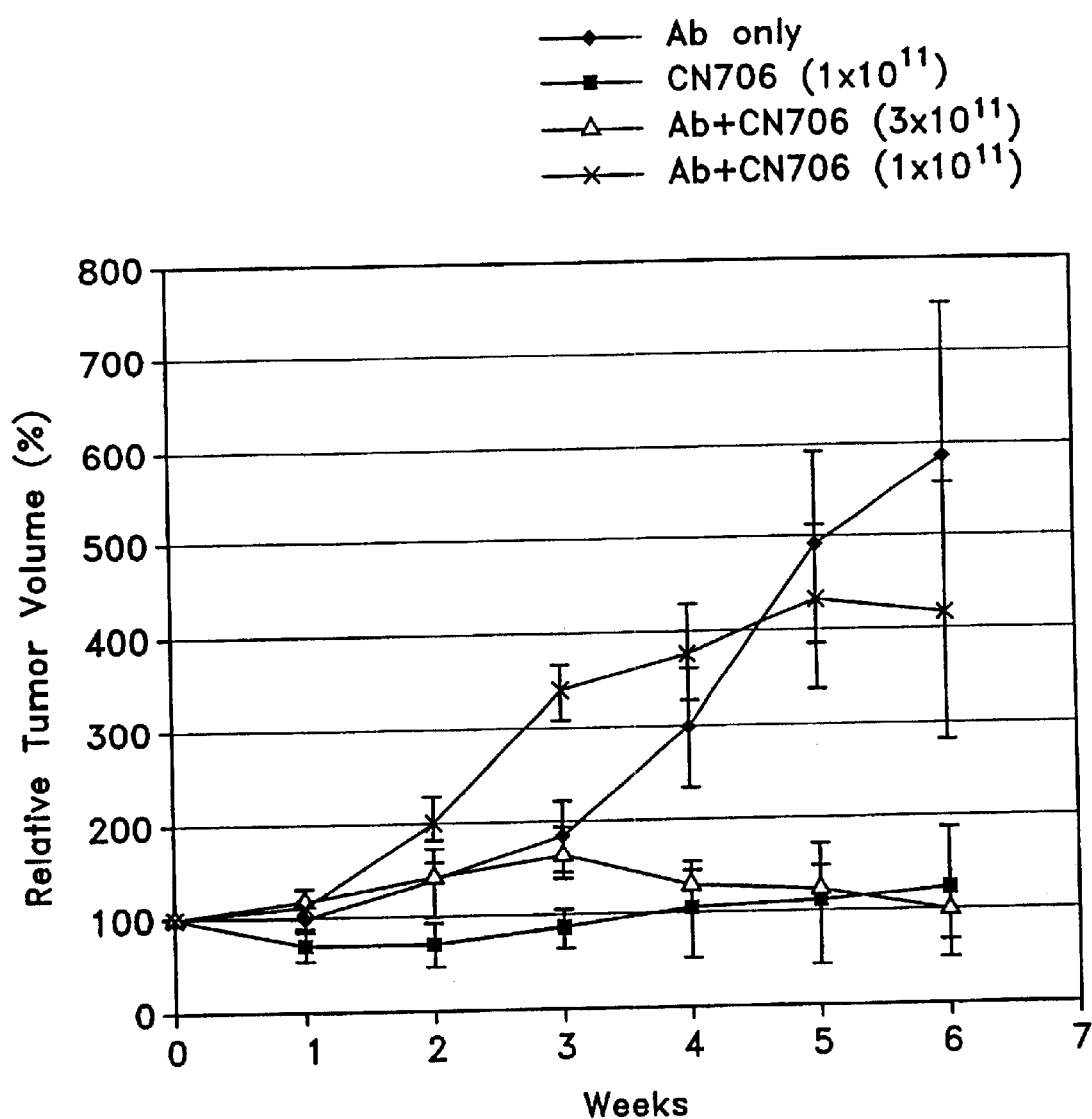
FIG. 3 is a graph depicting the effects of anti-adenovirus antibody (1:100) on the efficacy of a prostate-cell specific replication competent adenovirus (CN706) in nude mice bearing LNCaP tumors. Black line with diamond, antibody only; black line with square, virus (CN706) only; white line with triangle, antibody with CN706 ($3\times10^{11}$); black line with "x", antibody with CN706 ($1\times10^{11}$).
Figure 4:
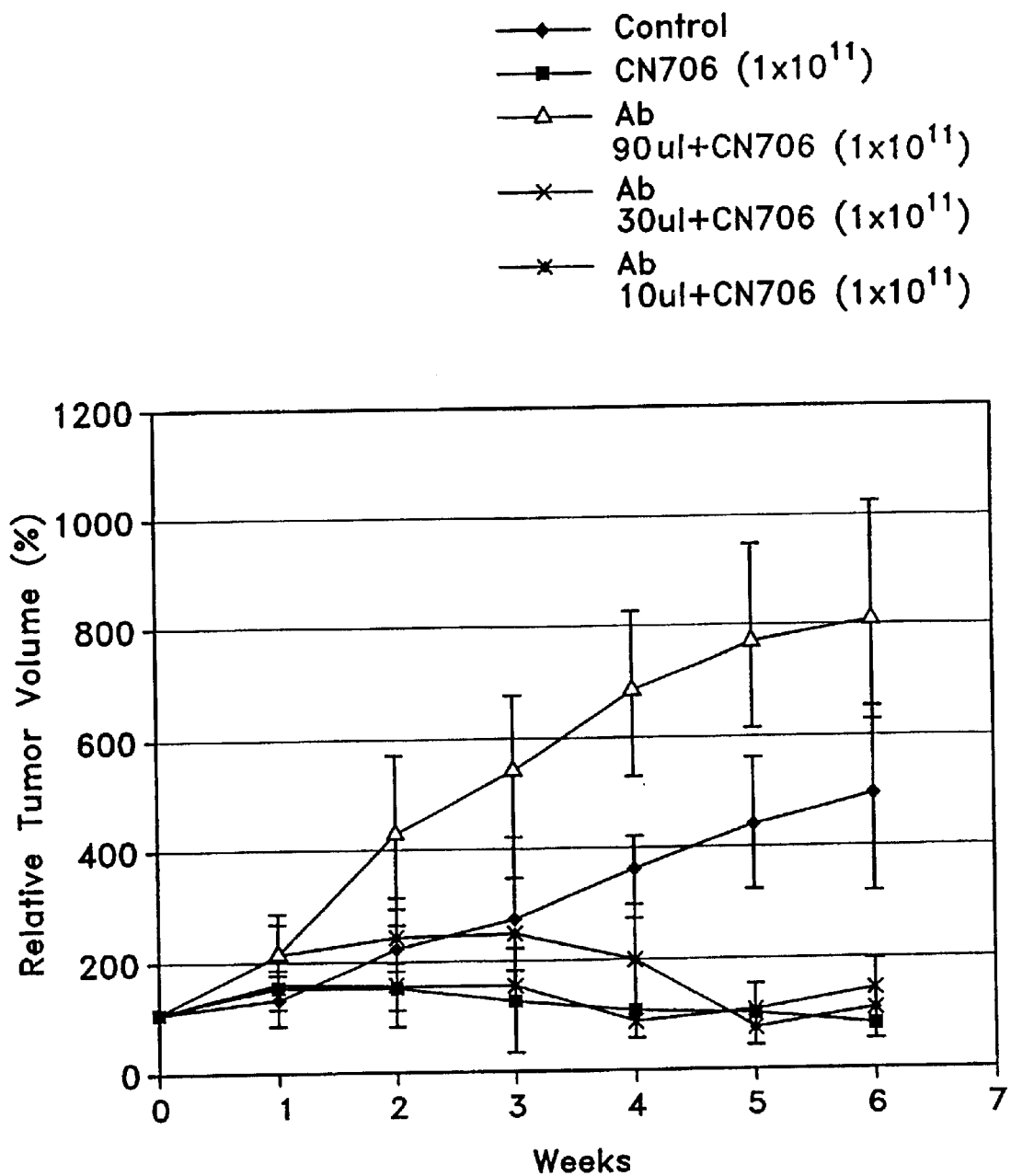
FIG. 4 is a graph depicting effects of neutralizing anti-adenovirus antibody titers on efficacy of CN706 in nude mice bearing LNCaP tumors. Black line with diamond, control; black line with square, CN706 ($1\times10^{11}$); white line with triangle, antibody (90 $\mu$l) plus CN706 ($1\times10^{11}$); black line with "x", antibody (30 $\mu$l) plus CN706 ($1\times10^{11}$); black line with star, antibody (10 $\mu$l) plus CN706 ($1\times10^{11}$).
Figure 8:
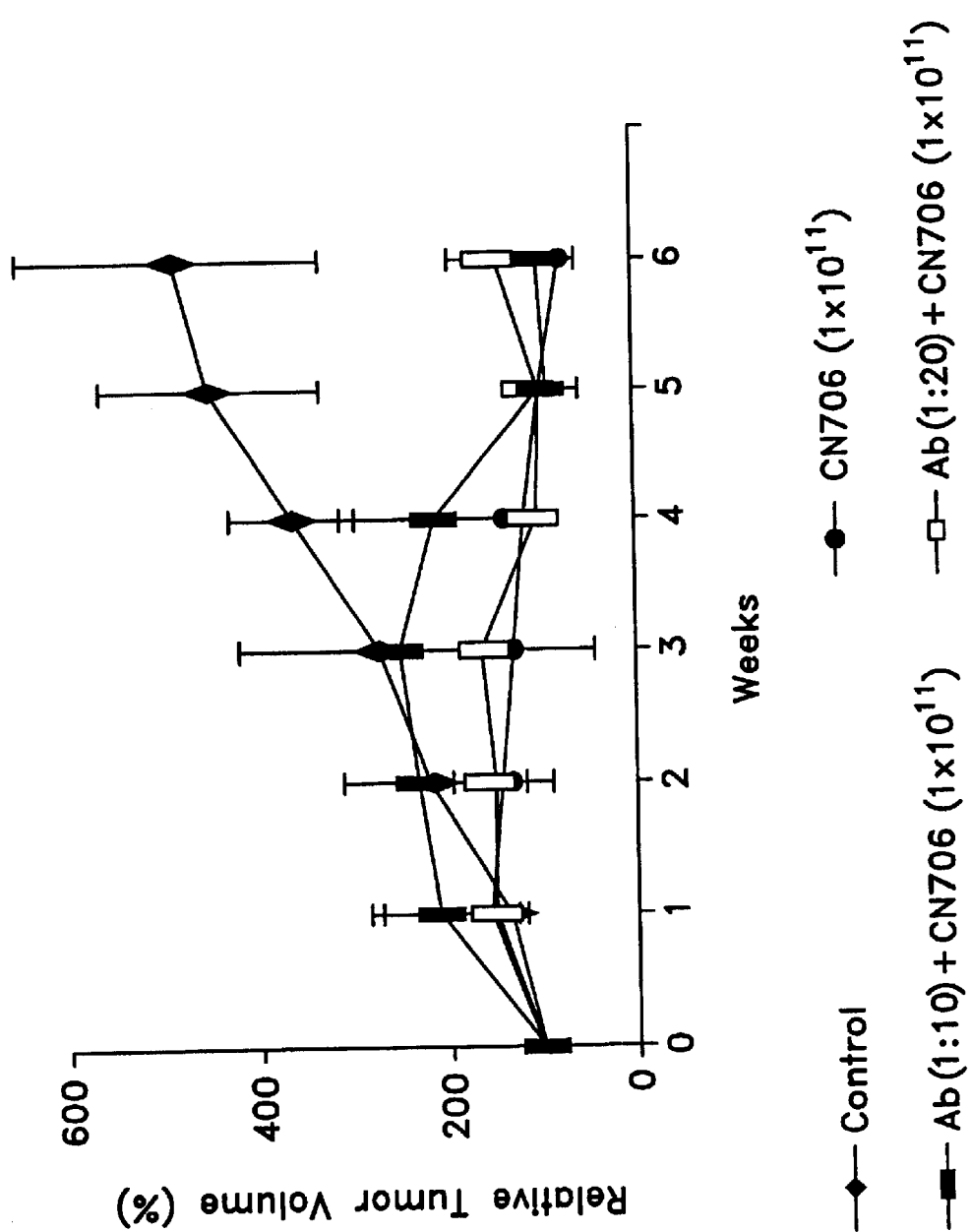
FIG. 8 is a graph depicting the effects of low titer anti-adenovirus antibody (1:20 to 1:10) on the efficacy of a prostate-cell specific replication competent adenovirus (CN706) in nude mice bearing LNCaP tumors. Black line with diamond, control; black line with circle, virus CN706 ($1\times10^{11}$) only; black line with solid square, antibody (1:10) with CN706 ($1\times10^{11}$); black line with open square, antibody (1:20) with CN706 ($1\times10^{11}$).

We have conducted several animal experiments that address pre-existing adenovirus immunity. We have observed that efficacy of anti-tumor treatments was greatly affected in the presence of high titer anti-adenovirus type 5 antibodies in our animal model following intravenous administration of a replication competent adenovirus that selectively replicates in prostate cells (FIG. 3). Effective therapy was achieved in the presence of low titer neutralizing anti-adenovirus type 5 antibodies or administration of a higher load of virus (FIGS. 4 and 8). Overall, these results from animal studies support the need for the development of a specific immunoadsorption system for the removal of anti-virus antibodies, such as anti-adenovirus antibodies, from patient blood, plasma or serum.

Presence of Neutralizing Antibodies in Patients with Prostate Cancer

We tested 28 prostatic patients' plasma for the presence of neutralizing anti-adenovirus type 5 antibodies, using whole adenoviral particles as antigen and Western blot analysis.

The results are shown in FIG. 1. Neutralizing antibodies were found in 13 of 28 samples (46%) with titers ranging from 1:5 (n=5) to 1:640 (n=1).

The nature of the specificity of the neutralizing antibody was assessed for three patients (two patients with 1:160 titer (#1 and #16), and one patient with no antibody titer (#1)) by assessing the molecular weight of the proteins that were identified by Western blot analysis. The results are shown in Table 1. Both patients with high titer displayed significant anti-penton activity. The patient with no anti-virus antibody activity showing specific reaction for anti-fiber indicates that this patient had previously been exposed to adenovirus. The failure to detect hexon and penton antibody in this patient could be an indication of decayed immunity.

TABLE 1

Molecular Basis of Anti-Adenovirus Activity

| Patient | Ab Titer | Anti-Penton | Anti-Fiber | Anti-Hexon |
|---|---|---|---|---|
| #1 | 1:160 | ++++ | +++ | + |
| #4 | 0 | +/− | ++++ | + |
| #16 | 1:160 | ++++ | + | + |

Development of an Animal Model with Pre-existing Anti-adenovirus Type 5 Antibodies To investigate the effect of pre-existing anti-adenovirus type 5 antibodies on the outcome of replication competent adenovirus based anti-tumor therapy, athymic BALB/c/nu/nu mice ("nude mice") were administered by intravenous injection purified anti-adenovirus type 5 neutralizing antibodies raised from rabbit. Nude mice are not immunocompetent, which is why they are extrinsically provided with anti-virus antibody. This is in contrast to a potential patient receiving adenoviral therapy who would be immunocompetent and would be able to mount a response to exposure to the adenoviral vector. The first blood sample was collected from the nude mice before injection of antibodies. Additional blood samples were collected at 1 hour, 4 hours, 8 hours, 12 hours, 24 hours, 48 hours, 5 days, 10 days, 15 days and 30 days after administration of antibodies.

Figure 2:
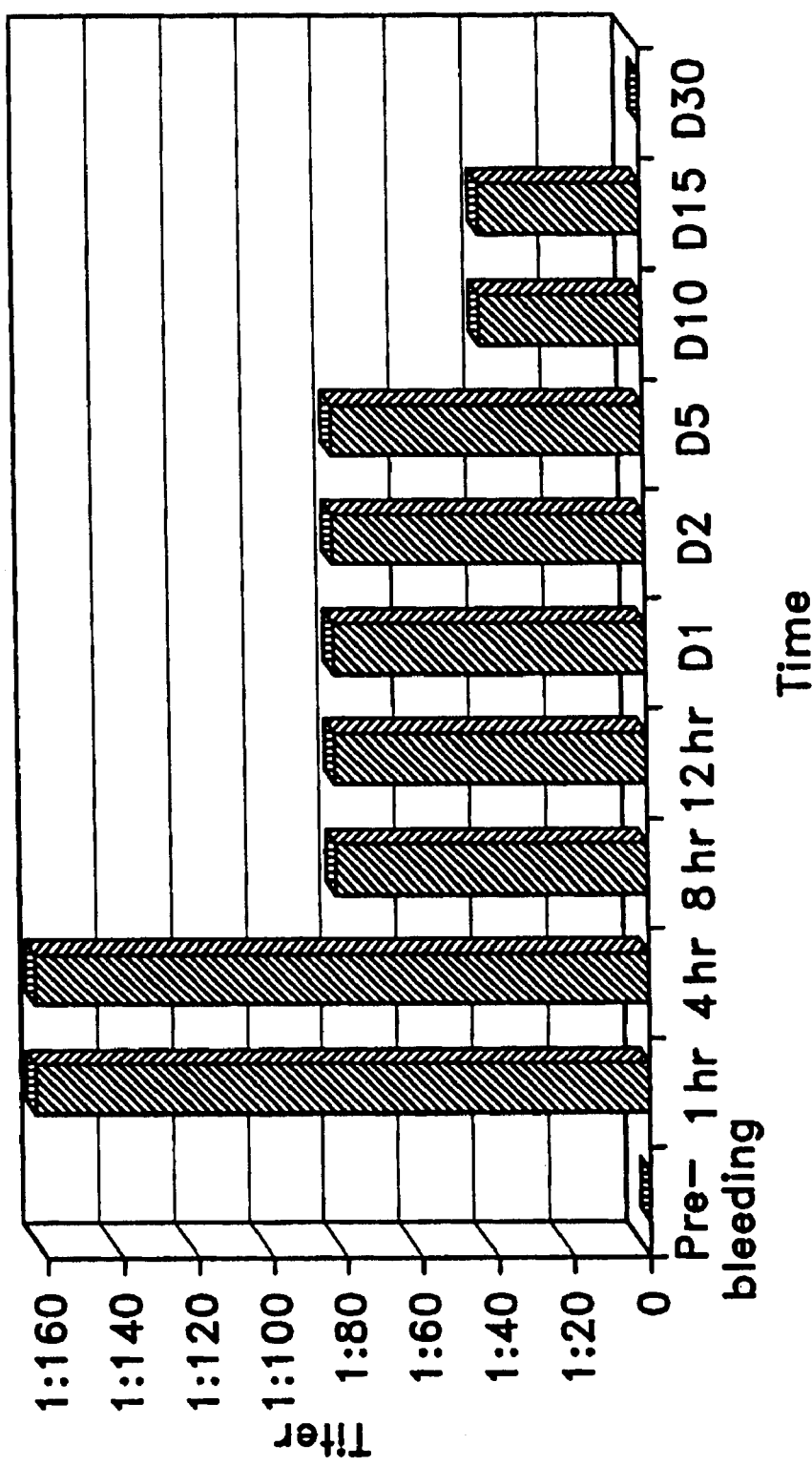
FIG. 2 is a bar graph depicting the time course of the presence of rabbit anti-adenovirus antibody in mouse. Athymic BALB/c/nu/nu mice received an intravenous injections of rabbit anti-adenovirus (serotype 5) antibody. At the depicted time points, blood samples were taken and antibody titers were measured by in vitro neutralizing assay.

Titers of anti-adenovirus type 5 antibodies from different time points were measured by in vitro neutralizing assay to determine stability of rabbit anti-adenovirus type 5 antibodies in blood circulation of nude mice. The neutralizing assay used was similar to that described in Gahery-Segard et al. (1997) Eur. J. Immunol. 27: 653–659. The results are shown in FIG. 2. A high level of circulating anti-adenovirus type 5 antibodies was present in nude mice 1 hour after administration of rabbit sera. This high level of antibodies was very stable in the first week of administration and started to decline on day 10. The titer of antibodies dropped to zero by day 30 after administration. Anti-adenovirus type 5 activity seems to be very specific since the blood sample from the zero time point did not show any antibody activity. Thus, passive administration of rabbit anti-adenovirus type 5 antibodies into nude mice produced a very good animal model for analyzing the effects of pre-existing immunity on the adenovirus therapy.

Protective Effect of Anti-virus Antibodies is Dependent on Titers of Anti-virus Antibodies in Blood Circulation To determine whether a higher dose of adenovirus can be tolerated in the presence of anti-virus antibodies, we have conducted a range-finding study by intravenous administration of CN706 (an attenuated, replication-competent adenovirus generated by inserting the prostate-specific antigen (PSA) promoter and enhancer transcription regulatory element (PSE-TRE) upstream of the E1A transcription unit in adenovirus serotype 5) into nude mice with pre-existing rabbit anti-Ad-5 antibodies. CN706 demonstrates selective cytotoxicity toward PSA expressing cells in vitro and in vivo. In the absence of anti-virus antibodies, all animals (n=4) were found dead after administration of $5 \times 10^{11}$ CN706 viral particles, which is 2.5 times the $LD_{50}$ dose found in nude mice. Typically a dose of $3 \times 10^{11}$ would be 100% lethal in nude mice. However, all animals appeared normal when the titer in the blood circulation ranged from 1:80 to 1:160 (Table 2). This demonstrates the significant effect anti-virus antibody may have on the efficacy of an adenoviral vector. Serum alanine aminotransferase (ALT) levels were also monitored for evaluating liver function of nude mice. In the group of animals without antibodies, a very high level of ALT could be detected (1,410 units) in blood circulation 24 hours after second dose injection. ALT levels reached to 12,650 units three days after second injection (Table 2). However, in the group of animals with antibodies, the level of ALT appears normal (Table 2). Thus, the presence of a higher degree of anti-adenovirus type 5 antibodies protects animals from typically lethal doses of adenovirus in nude mice.

TABLE 2

Toxicity Study in Nude Mice Intravenously Administered CN706 With and Without Pre-Existing Anti-Adenovirus Type 5 Antibodies

| Group | Treatment Regimen | Clinical Condition | ALT in Day 2 | ALT in Day 5 | ALT in Day 15 |
|---|---|---|---|---|---|
| 1 | Rabbit anti-adenovirus type 5 Ab (1:80 to 1:160) | Animals appeared healthy for the duration of the experiment | — | — | — |
| 2 | CN706 $5 \times 10^{11}$ particles | All animals were found to be dead on day 5 | 1410 | 12650 | |
| 3 | Rabbit anti-adenovirus type 5 Ab (1:80 to 1:160), CN706 $5 \times 10^{11}$ particles | Animals appeared healthy for the duration of the experiment | 230 | 60 | 160 |
| 4 | Rabbit anti-adenovirus type 5 Ab (1:80 to 1:160), CN706 $3 \times 10^{11}$ particles | Animals appeared healthy for the duration of the experiment | 105 | 35 | 55 |
| 5 | Rabbit anti-adenovirus type 5 Ab (1:80 to 1:160), CN706 $1 \times 10^{11}$ particles | Animals appeared healthy for the duration of the experiment | 100 | 45 | 35 |

We also tested the protective effect for adenovirus in the presence of low titers of anti-adenovirus antibodies by comparing animal survival and level of ALT in blood in immuno-incompetent nude mice. All animals with low titers of antibodies (1:10) died after receiving $2.5 \times 10^{11}$ particles of CN706 (a dose greater than the $LD_{50}$ dose), whereas animals with high titers of antibodies (1:80) appeared normal after receiving $2.5 \times 10^{11}$ particles of CN706. No infectious viral particles were found in the blood samples day 2, day 3, day 4, day 5 and day 6 after intravenous injection of CN706. This demonstrates that even a moderate amount of antibody is able to quickly neutralize a relatively high dose of viral particles. ALT reached a very high level (Day 2: 1,955 units, Day 3: 13,450 units) in the group of animals with low titers of antibodies. In contrast, ALT appeared to be within normal range in the group of animals with high titers of antibodies (Table 2). Thus, the protective effect of anti-virus antibodies is dose-dependent fashion, with higher titers of antibodies (1:80–1:160) protecting animals from a dose of adenovirus greater than the $LD_{50}$ dose, whereas lower titers of antibodies (1:10) appeared to have no protective effect. These results indicate the effects of anti-virus antibodies on the clearance of a therapeutic viral vector. These results also indicate that the level of anti-virus antibody, especially anti-adenovirus antibody, that is recommended for efficacious therapy using adenovirus should be less than about 1:80.

It is important to note that unlike nude mice, human patients would be immuno-competent and be able to raise more antibodies in response to the presence of adenovirus in the circulation. Therefore, a dose of adenovirus that would be lethal in a nude mouse would not necessarily indicate lethality in a human.

infectious viral particles were lost from blood circulation of mice in the first 24 hours after administration. Additionally, the time-dependent pattern of this loss was found in animals with pre-existing antibodies. In mice with an antibody titer of 1:10, infectious viral particles were $1.2 \times 10^5$ $TCID_{50}$ units 4 hours after administration of $2.5 \times 10^{11}$ particles of CN706, while at 24 hours only 0.3% ($3.75 \times 10^2$ $TCID_{50}$ units) of the amount of active viruses were present in blood circulation. In mice with a high titer of antibodies (1:80), infectious viral particles were $3.7 \times 10^2$ $TCID_{50}$ units 4 hours after administration of $2.5 \times 10^{11}$ particles of CN706, which was 1000 fold less than that of mice in the absence of antibodies. These experiments demonstrate how efficient anti-virus antibodies are at clearing the circulation of virus. Without selective removal of anti-virus antibody in an immunocompetent individual, relatively low levels of anti-virus antibody would be able to clear viral vector rather quickly thereby decreasing its therapeutic value.

TABLE 3

Plasma ALT Concentration in Nude Mice Intravenously Administered CN706 With and Without Rabbit Anti-Adenovirus Type 5 Antibody

| Group | Treatment Regimen | Clinical Condition | ALT in Day 1–2* | ALT in Day 2 | ALT in Day 3 | ALT in Day 4 | ALT in Day 5 |
|---|---|---|---|---|---|---|---|
| 1 | CN706, $2.5 \times 10^{11}$ | Animals died on day 3 | 175 | 2700 | 19150 | | |
| 5 | Ab, 1:80 CN706, $2.5 \times 10^{11}$ | Animals appear health | N/A | 450 | 150 | 85 | 55 |
| 8 | Ab, 1:20 CN706, $2.5 \times 10^{11}$ | Animals died on day 6 | 105 | 1955 | 13450 | 14600 | 10400 |

Difference of the Infectious Adenoviral Particles in Blood Circulation of Nude Mice in the Presence and Absence of Anti-adenovirus Type 5 Antibodies To determine the half-life of infectious adenoviral particles in the blood circulation of nude mice in the presence and absence of anti-virus antibodies, we conducted a $TCID_{50}$ assay to quantitate active viruses from blood samples of nude mice. Blood samples from different time points were collected from animals with and without pre-existing rabbit anti-adenovirus type 5 antibodies, after intravenous administration of CN706, and infectious viral particles were detected by $TCID_{50}$ assay. The results from $TCID_{50}$ (Table 3) indicated that the amount of active virus in the blood circulation showed a steady decline over the first 24 hours after intravenous administration of $2.5 \times 10^{11}$ particles of CN706. At 4 hours, infectious viral particles were $3.75 \times 10^5$ $TCID_{50}$ units, and at 24 hours only 0.2% ($7.2 \times 10^2$ $TCID_{50}$ units) of the amount was present at 4 hours was detected. A similar pattern of loss of active adenovirus in blood circulation was observed in animals receiving $2.5 \times 10^{10}$, $2.5 \times 10^9$, and $2.5 \times 10^8$ particles of CN706, respectively, with the relative less amounts at each time point parallel to that with $2.5 \times 10^{11}$ particles, in a dose-dependent fashion. Thus, it appears that more than 99.5% of

TABLE 4

Detection of Infectious Viral Particles by $TCID_{50}$ Assay in Blood Samples of Nude Mice

| Group | Treatment Regimen | Titers of pre-existing neutralizing Ab | $TCID_{50}$ Unit, 4 hrs after Injection of CN706 | $TCID_{50}$ Unit, 24 hrs Injection of CN706 |
|---|---|---|---|---|
| 1 | Day 1, i.v. injection of CN706 $2.5 \times 10^{11}$ particles | 0 | $3.65 \times 10^5$ unit/ml | $7.2 \times 10^2$ unit/ml |
| 2 | Day 1, i.v. injection of CN706 $2.5 \times 10^{10}$ particles | 0 | $6 \times 10^4$ unit/ml | $2.4 \times 10^2$ unit/ml |
| 3 | Day 1, i.v. injection of CN706 $2.5 \times 10^9$ particles | 0 | $1.5 \times 10^3$ unit/ml | ND |
| 4 | Day 1, i.v. injection of CN706 $2.5 \times 10^8$ particles | 0 | $6 \times 10^2$ unit/ml | ND |
| 5 | Day 0, i.v. injection of rabbit anti-adenovirus type 5 Ab 0.18 mg, Day 1, i.v. injection CN706 $2.5 \times 10^{11}$ particles | 1:80 | $3.7 \times 10^2$ unit/ml | ND |

TABLE 4-continued

Detection of Infectious Viral Particles by TCID$_{50}$ Assay in Blood Samples of Nude Mice

| Group | Treatment Regimen | Titers of pre-existing neutralizing Ab | TCID$_{50}$ Unit, 4 hrs after Injection of CN706 | TCID$_{50}$ Unit, 24 hrs Injection of CN706 |
|---|---|---|---|---|
| 6 | Day 0, i.v. injection of rabbit anti-adenovirus type 5 Ab 0.045 mg, Day 1, i.v. injection CN706 2.5 × 10$^{11}$ particles | 1:20 | 3 × 10$^4$ unit/ml | ND |
| 7 | Day 0, i.v. injection of rabbit anti-adenovirus type 5 Ab 0.023 mg, Day 1, i.v. injection CN706 2.5 × 10$^{11}$ particles | 1:10 | 1.2 × 10$^5$ unit/ml | 3.75 × 10$^2$ units/ml |

Effects of Anti-adenovirus Type 5 Antibodies on the Efficacy of Intravenously Administered CN706 in Nude Mice Bearing LNCaP Tumors To determine the effect of pre-existing anti-virus antibodies on the outcome of replication competent adenovirus based anti-tumor therapy, BALB/c nu/nu mice bearing LNCaP tumors injected with LNCaP cells suspended in 50% MEM medium and 50% Matrigel subcutaneously between the scapulas. Four weeks after transplantation, animals with palpable tumors were intravenously injected with rabbit anti-adenovirus type 5 antibodies to establish a condition mimicking pre-existing antibodies in the blood circulation. Titers of anti-adenovirus type 5 antibodies in these animals were about 1:80–1:160. One day following administration of antibodies, CN706 was introduced into nude mice by intravenous injection. Tumor volumes were measured weekly. Tumors in the group treated with 1×10$^{11}$ particles of CN706 without pre-existing antibody displayed significantly inhibited growth of the tumors, whereas the group treated with the same amount of CN706 plus pre-existing antibody at a titer of 1:100 showed significant growth of the tumor. However, at the same level of the pre-existing antibody, tumor growth was significantly inhibited when the CN706 dose was increased 3-fold up to 3×10$^{11}$ particles per animal. (FIG. 3). Thus, pre-existing anti-virus antibodies appeared to reduce efficacy of the viral therapeutic agent.

The effect was further studied by varying antibody titers. A fixed dose of CN706 (1×10$^{11}$) was delivered into animals with three different neutralizing antibody titers (1:10, 1:20, 1:80). Anti-tumor effects were determined by measuring tumor volumes weekly. The results are shown in FIG. 4. Tumors in animals with higher titers of antibodies and control group grew progressively, whereas growth of the tumors in animals with lower titers of antibodies was inhibited following treatment (FIG. 8). The therapeutic efficacy in these animals is equivalent to that of animals treated with CN706 alone. Thus, it appears that lower titers of pre-existing antibodies to adenovirus type 5 did not inhibit the efficacy of adenovirus treatment in our animal model.

Figure 5:
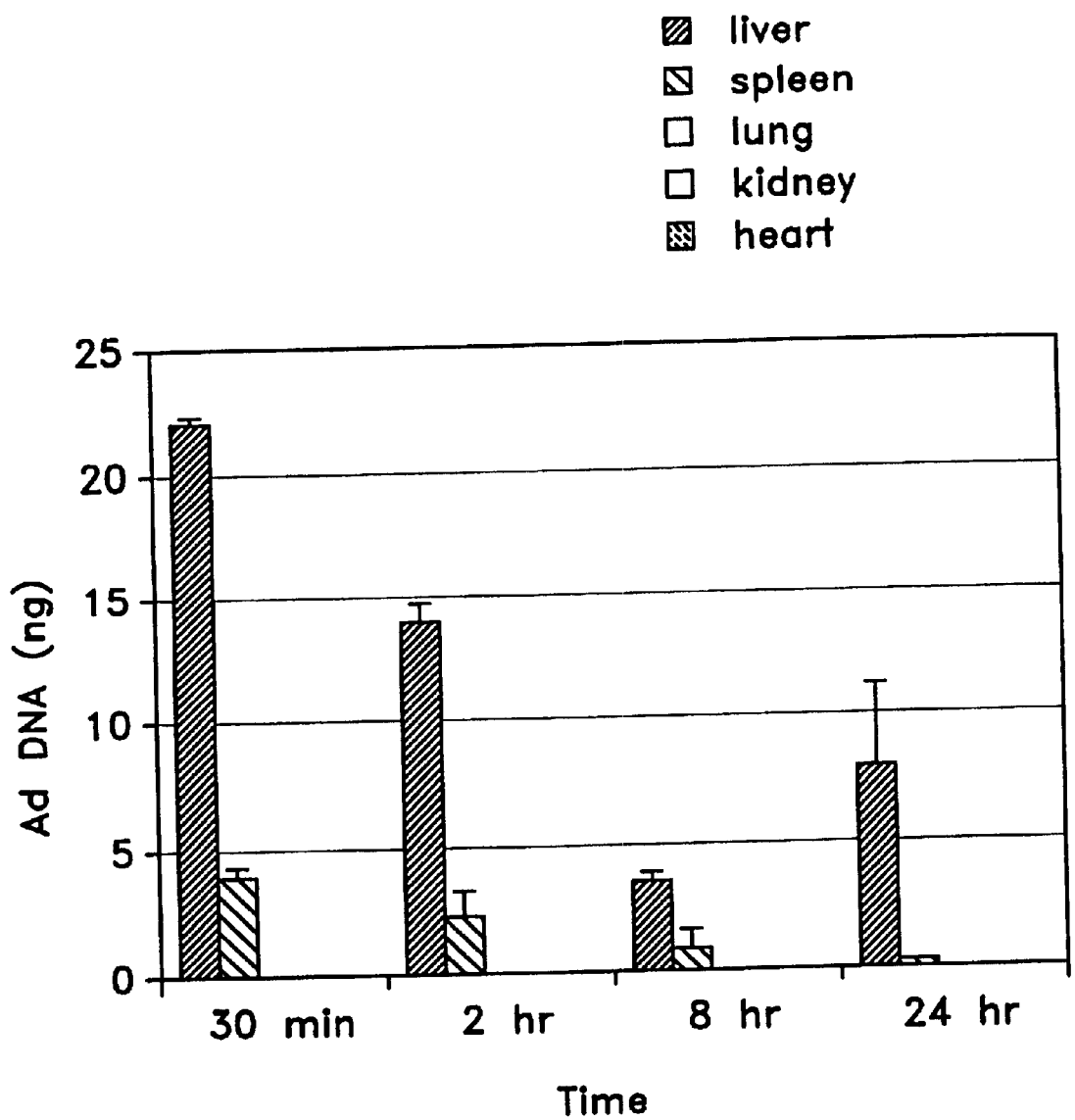
FIG. 5 is a bar graph depicting amounts of adenovirus DNA in various organs (of nude mice) after intravenous administration of CN706 ($2.5\times10^{11}$). Error bars are shown.

Analysis of Adenovirus Dissemination and Distribution Following IV Administration We evaluated the biodistribution of adenovirus after intravenous administration. CN706 virus (2.5×10$^{11}$ particles) was administered to nude mice intravenously, and we analyzed the presence of adenovirus DNA in various organs (liver, spleen, lung, kidney, heart) after various time points by slot blot analysis using E4 DNA as probe. Two mice were tested for each time point. The results are shown in FIG. 5. The liver harbored the greatest amount of adenoviral DNA, followed by the spleen. The other organs had negligible amounts of adenoviral DNA.

Figure 6:
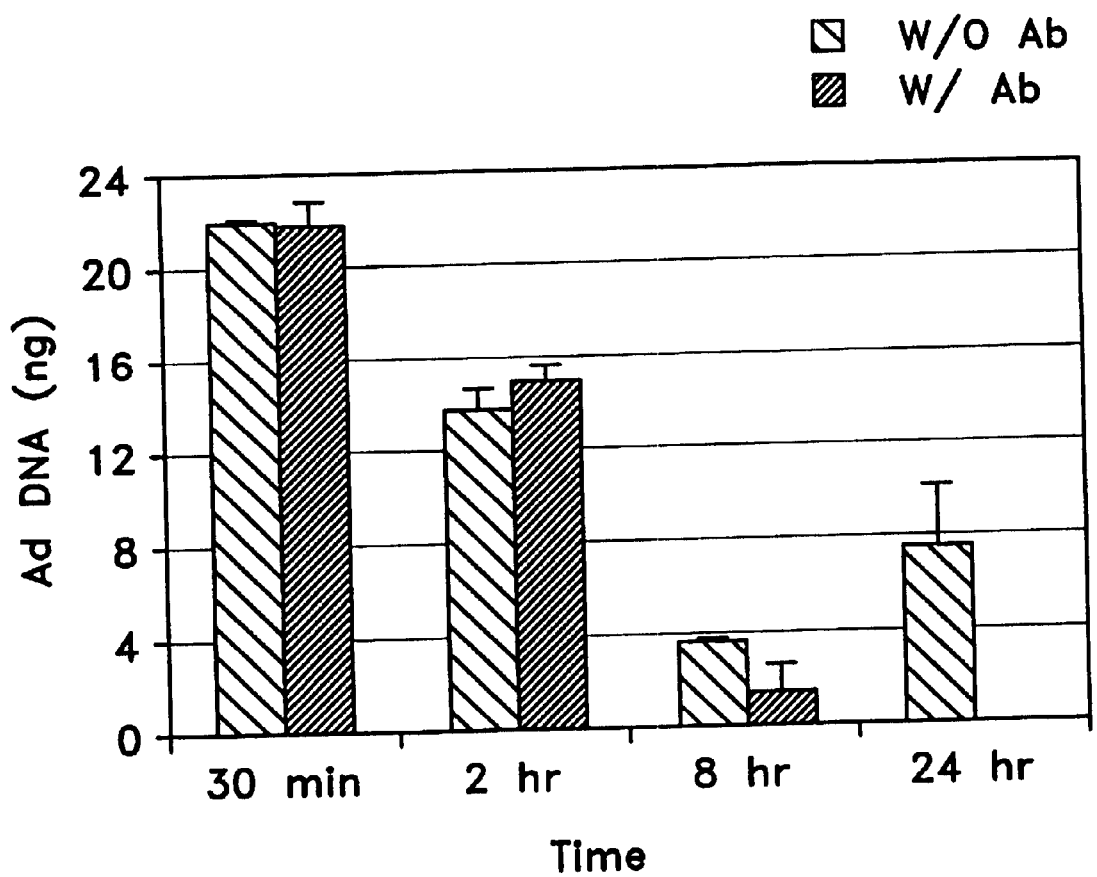
FIG. 6 is a bar graph depicting amounts of adenovirus DNA in liver (of nude mice) after administration of CN706 ($2.5\times10^{11}$), with or without pre-administered anti-adenovirus antibody. The left-hand bars represent mice without antibody; the right-hand bars represent mice with antibody.

Evaluation of Retention of Adenovirus in Liver in Mice with and without Anti-adenovirus Antibody CN706 (2.5×10$^{11}$ particles) was administered intravenously to nude mice with and without pre-administered anti-adenovirus antibody (1:80). Adenovirus DNA was measured in liver (as described above) at various timepoints after adenovirus administration by slot blot analysis (two mice for each timepoint). The results are shown in FIG. 6. The amount of adenovirus DNA was very similar between mice with and without pre-existing antibody at 30 minutes and 2 hours following adenoviral administration. However, at 24 hours, mice without pre-administered antibody still showed significant levels of adenovirus, while no significant amount of adenovirus DNA was found in mice with pre-existing antibody. We also found that no significant amount of adenovirus DNA was detected in other organs, such as lung, heart, kidney and blood, suggesting that rapid loss of adenovirus DNA in liver in mice with pre-existing antibody is not due to virus redistribution. The rapid loss of adenovirus DNA from liver in mice with pre-existing antibody may explain why animals with pre-administered antibody can tolerate higher viral dose (LD dose) than mice without pre-existing antibody.

Evaluation of Impact on Tumor Growth of Antibody Administered after Administration of Adenovirus To determine the effect of post-existing anti-adenovirus antibodies to adenovirus on anti-tumor efficacy of adenoviral vectors, rabbit anti-adenovirus antibodies were injected intravenously injected into nude mice on days 14 and 15 after administration of CN706 (1×10$^{11}$ particles). A high titer of antibody (1:300) was observed on day 15 post-administration of CN706.

Figure 7:
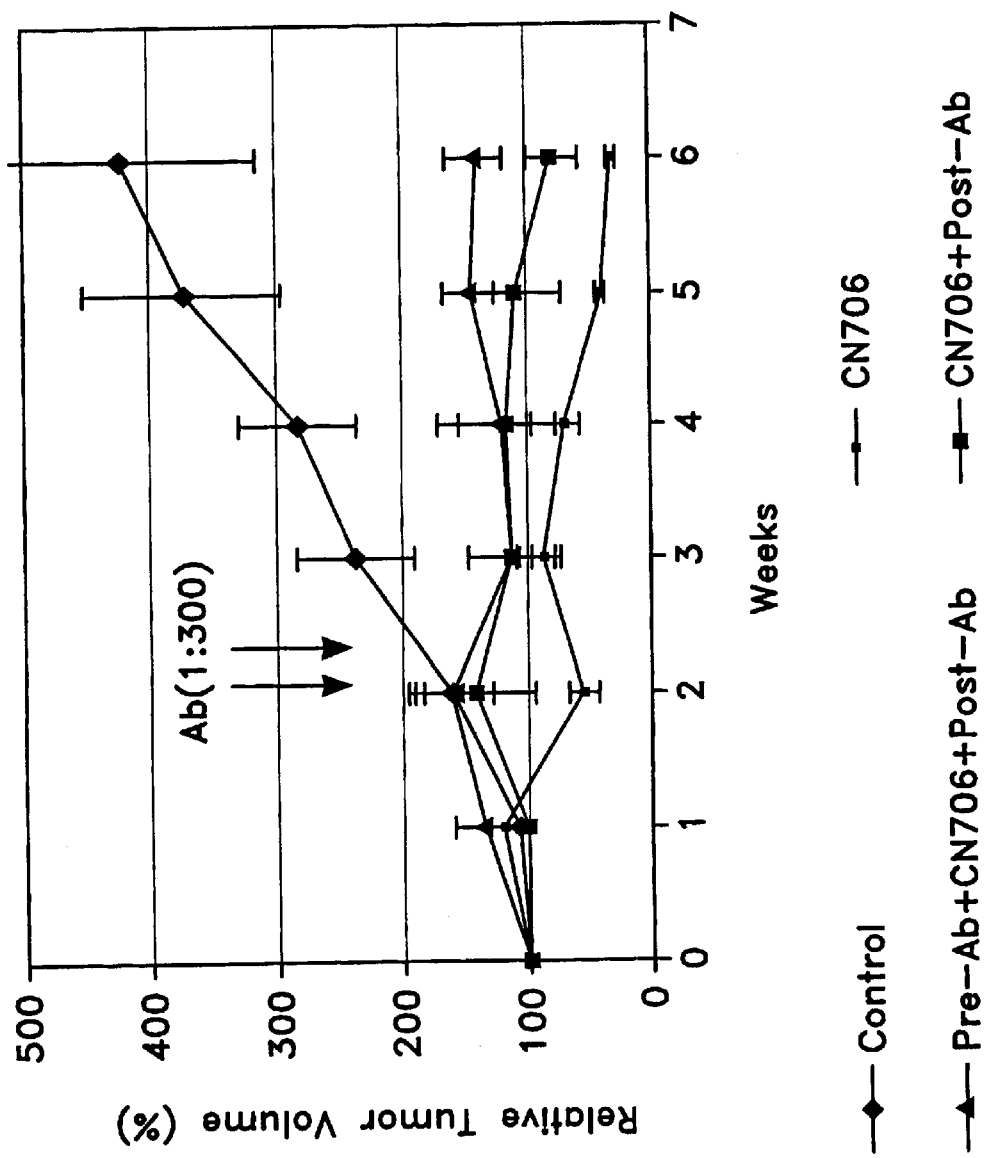
FIG. 7 is a graph depicting relative tumor volume in mice receiving CN706 as well as antibody (triangle) administered week 2 after viral injection.

The results are shown in FIG. 7. Post-administered antibody did not appear to have a significant negative impact on CN706's ability to suppress tumor growth, suggesting that as long as viral replication is allowed to commence (i.e., in target tissue such as tumor), anti-viral antibody in blood circulation does not eliminate anti-tumor efficacy of the viral vector.

Example 2

Anti-Adenovirus-Antibody Removal Using an Affinity Column

Prior to commencing the procedure to remove anti-adenovirus antibody from the individual a small sample of blood is taken in order to determine the titer of the anti-adenovirus antibody.

Adenovirus fiber and/or penton protein immunosorbents are prepared by amplifying genes encoding for the fiber and penton proteins using polymerase chain reaction (PCR) from adenovirus. The genetic material is then cloned into a recombinant baculovirus expression system. Baculovirus is then used to infect an insect cell line, SF9 (Invitrogen, Carlsbad, Calif.), which produces the adenovirus proteins. The proteins are purified using methods known in the art and diluted in bicarbonate buffer.

The affinity column is prepared as follows. A coupling solution that is applied to the activated matrix is prepared by dissolving an adenovirus fiber and/or penton protein in a concentration of 5 mg/ml in sterile bicarbonate buffer pH 8.3. The coupling solution is stored at 4° C. until needed. The washing solution used to swell, wash and activate the matrix is 4–6 L of sterile 1 mM HCl at 4° C. Approximately 400 ml CNBr-activated Sepharose 4 Fast Flow Matrix (Pharmacia Biotech, Piscataway, N.J.) is washed initially with 10–15 volumes of 1 mM HCl allowing the mixture to equilibrate for 10–15 minutes with each wash. The activated matrix is mixed with the previously prepared coupling solution, incubating the mixture at room temperature for 2 hours with stirring with a glass rod every 10 minutes or incubating overnight at 4° C. with gentle agitation. After coupling, non-reacted groups are blocked on the matrix using Tris buffer or ethanolamine for a few hours. The coupled medium is washed using alternate low and high pH, acetate pH 3–4 or Tris HCl pH 8–9. Washing is with 3 volumes Tris, then with 3 volumes acetate, and the Tris/acetate wash is repeated 3 times. A column is packed using a pump in the same conditions as that will be used to later load the plasma to ensure homogenous packing. Literature and instructions accompanying the column and the Sepharose should be referenced for details on packing the column. The column is equilibrated using saline at physiological pH.

Blood is obtained using a 17 gauge needle and anticoagulated using heparin and sodium citrate, and plasma is obtained by centrifugation.

Plasma is serially pumped into two glass columns (XK 50/20 column; Pharmacia Biotech, Piscataway, N.J.) with a volume of 275 ml each containing CNBr-activated Sepharose 4 Fast Flow Matrix coupled to either adenovirus fiber protein and/or penton protein. Adenovirus neutralizing antibody present in the plasma is removed upon binding to the adenovirus proteins linked to the solid phase matrix of the column. Plasma and blood cells are returned to the individual via a second venous access. A small sample of blood or plasma eluted from the columns is tested for antibody titer. The columns are regenerated as described in methods of Richter et al. (1997) *ASAIO* 43(1):53–59.

Example 3

Removal of Anti-Adenovirus-Antibody Using Various Affinity Columns

We have tested a number of immunosorbents and compared their abilities to remove anti-adenovirus antibodies from human plasma. These immunosorbents include protein A, and adenoviral hexon, penton, fiber proteins used alone or used all together.

Figure 12:
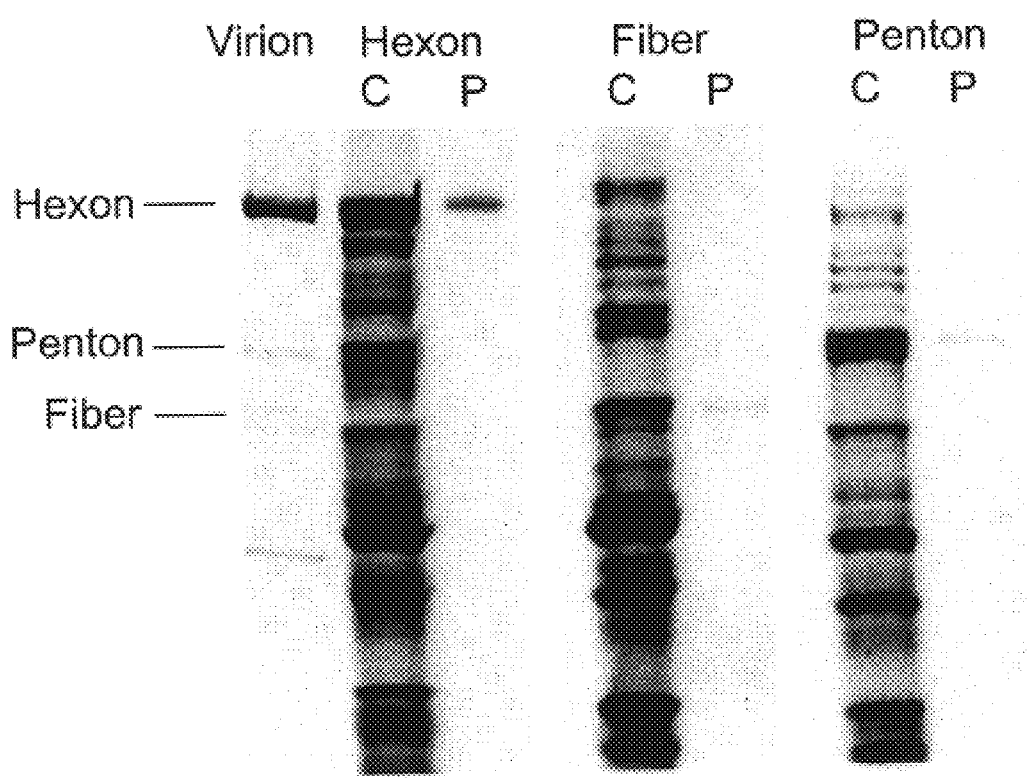
FIG. 12 is a reproduction of an immunoblot showing the expression and purity of the recombinant hexon, penton and fiber proteins from *E. coli*. Lane "C" denotes crude extracts; lane "P" denotes purified sample.

6×Histidine tagged adenovirus hexon, fiber or penton protein immunosorbents were prepared by amplifying genes encoding these proteins using 6×Histidine linker primers. The genetic material was then introduced into *E. coli* for protein expression. The *E. coli* expressed adenovirus hexon, fiber or penton proteins were then purified according to the manufacturer's instructions (QIA express systems from Qiagen). Electrophoresis of total *E. coli* lysates and purified fractions confirmed the abundance and purity of the recombinant hexon, fiber and penton proteins (see FIG. 12).

Figure 15:
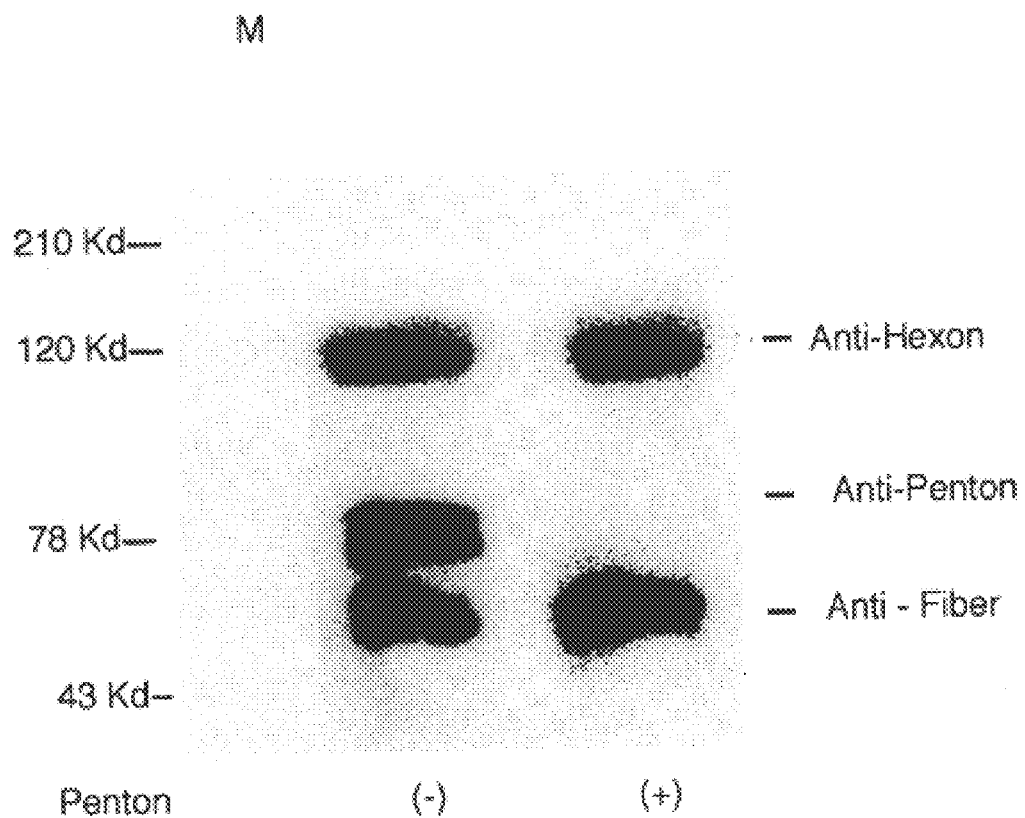
FIG. 15 is an immunoblot showing the depletion of anti-penton antibodies from human plasma using penton-affinity column. Penton protein was detected prior to (lane (−)) and not after (lane (+)) affinity chromatography.
Figure 16:
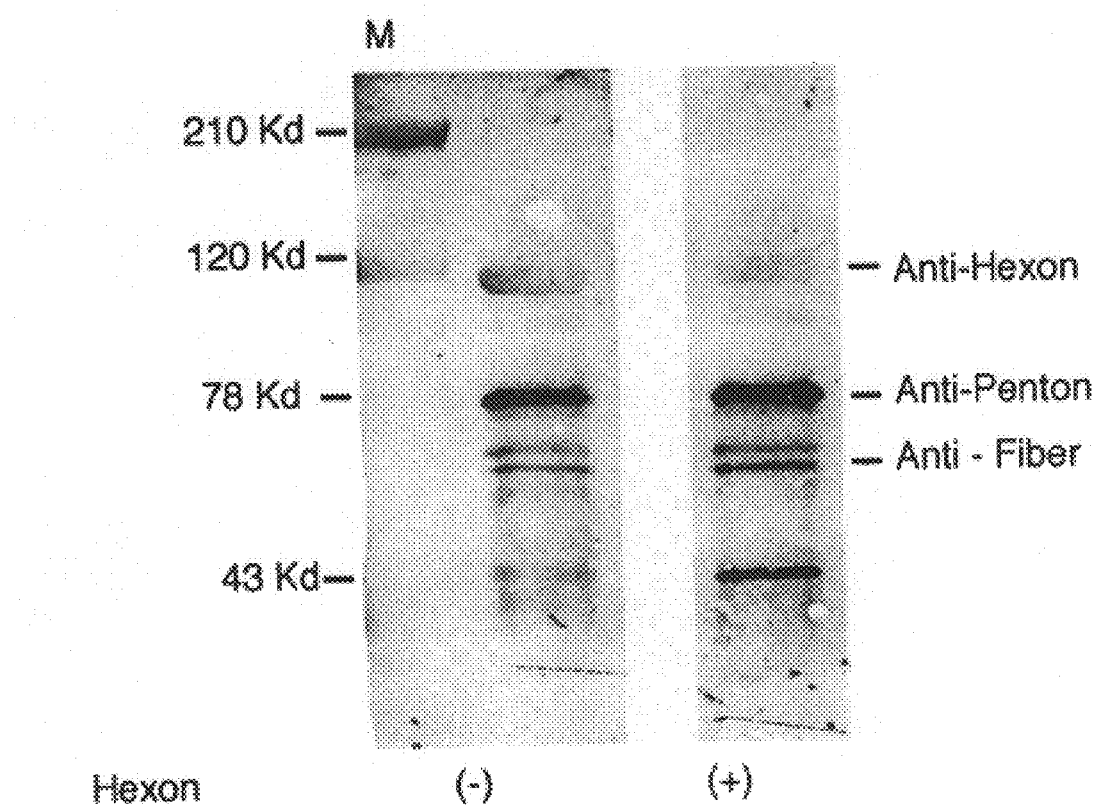
FIG. 16 is an immunoblot showing the removal of anti-hexon antibodies from human plasma lysate using hexon-affinity column. Hexon protein was detected prior to (lane (−)) and not after (lane (+)) affinity chromatography.
Figure 17:
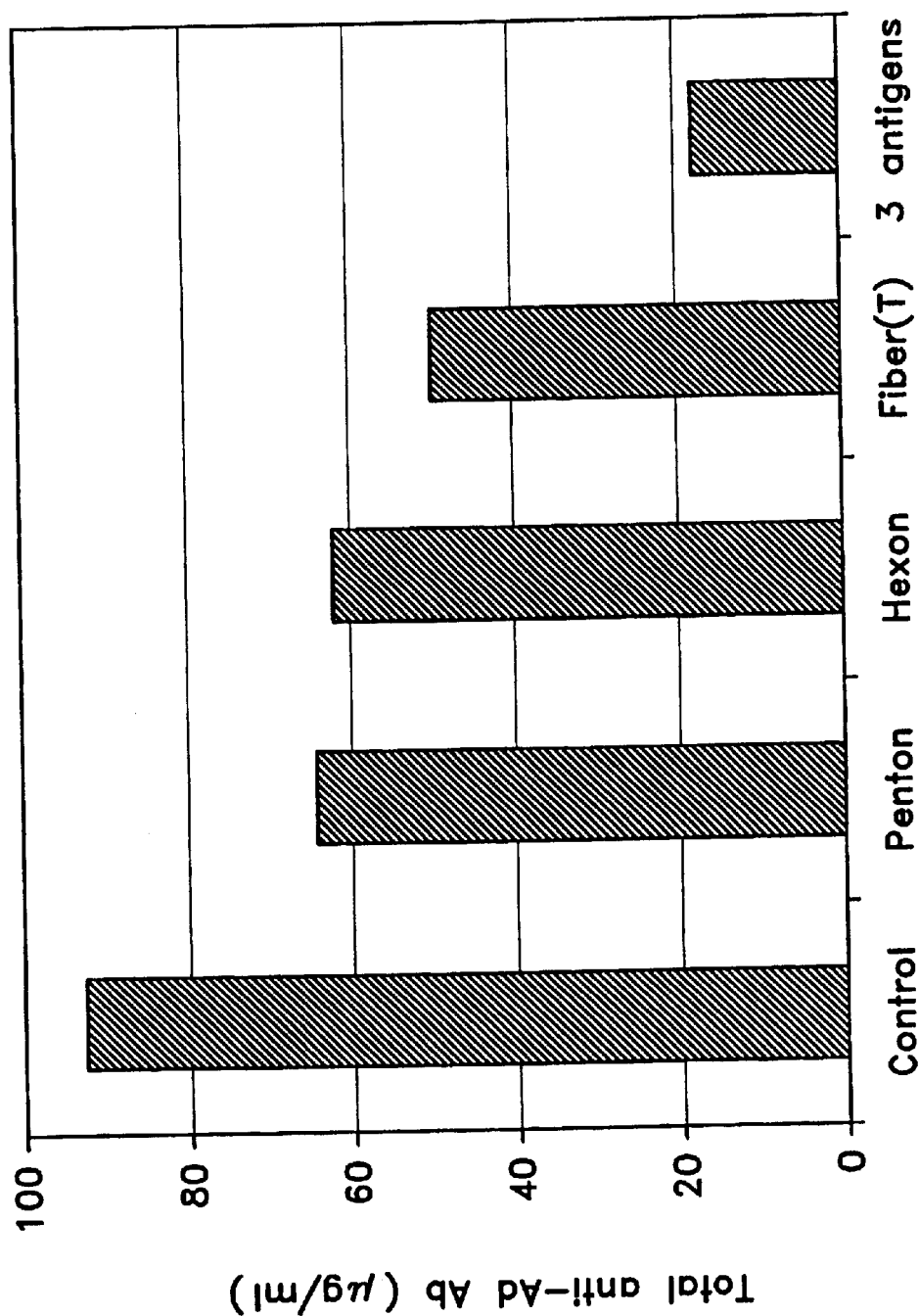
FIG. 17 is a bar graph depicting the relative efficiencies of various immunosorbents in clearing total anti-adenovirus antibody from normal human plasma (HS0331) which has a high pre-existing neutralizing antibody titer. Normal human plasma was obtained from a non-cancerous patient.
Figure 18:
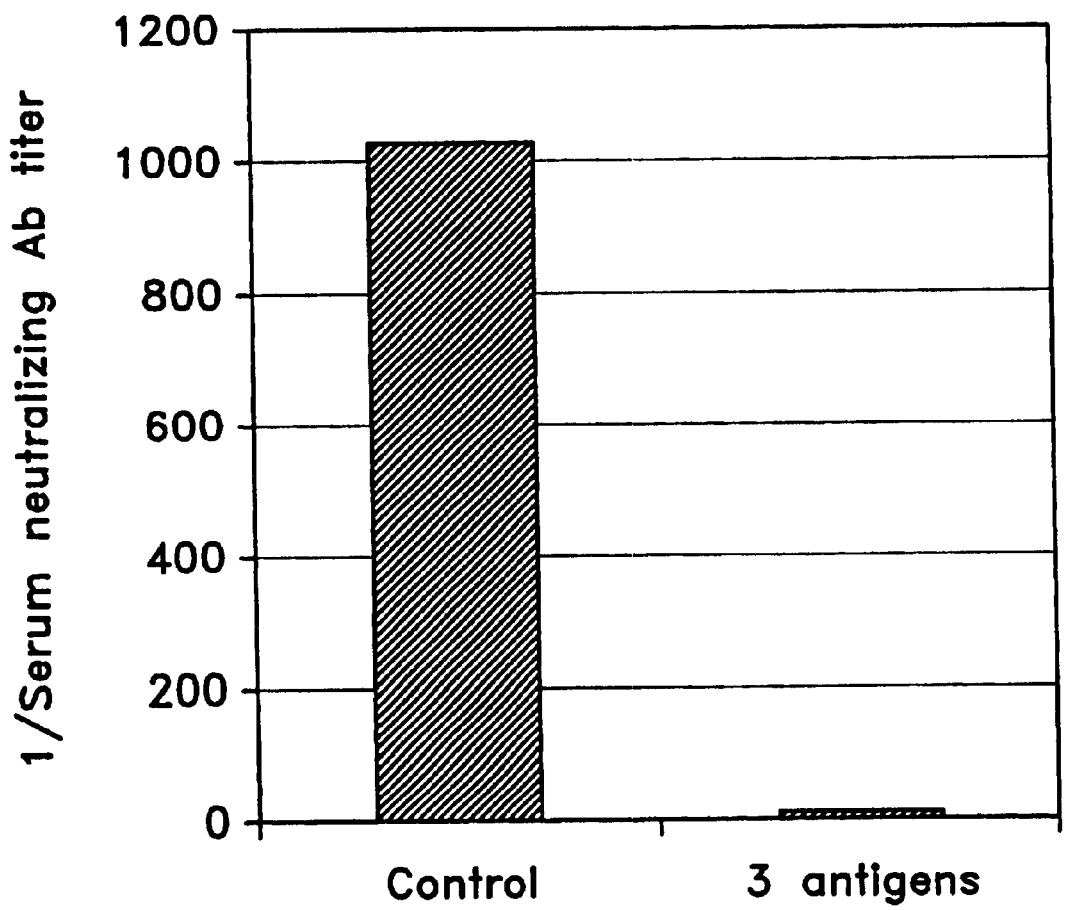
FIG. 18 is a bar graph depicting the depletion of neutralizing antibody activities present in normal human plasma (HS0331) using an affinity column packed with a mixture of immunosorbents hexon, penton and fiber proteins. Normal human plasma was obtained from a non-cancerous patient.
Figure 19:
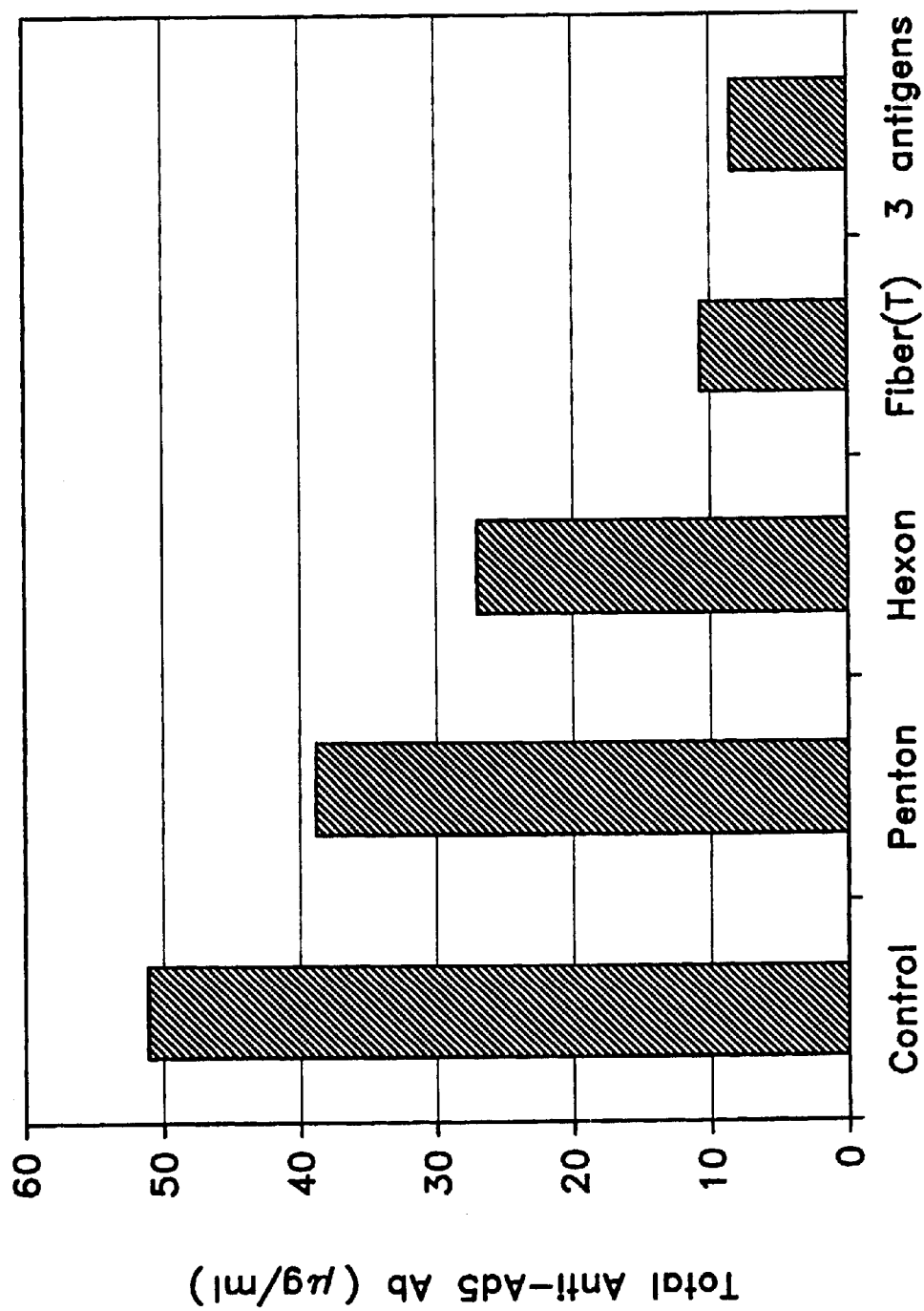
FIG. 19 is a bar graph depicting the relative efficiencies of various immunosorbents in clearing total anti-adenovirus antibody from a CN706 patient's plasma (GG/003), which was collected 15 days after injecting the therapeutic adenovirus CN706.
Figure 20:
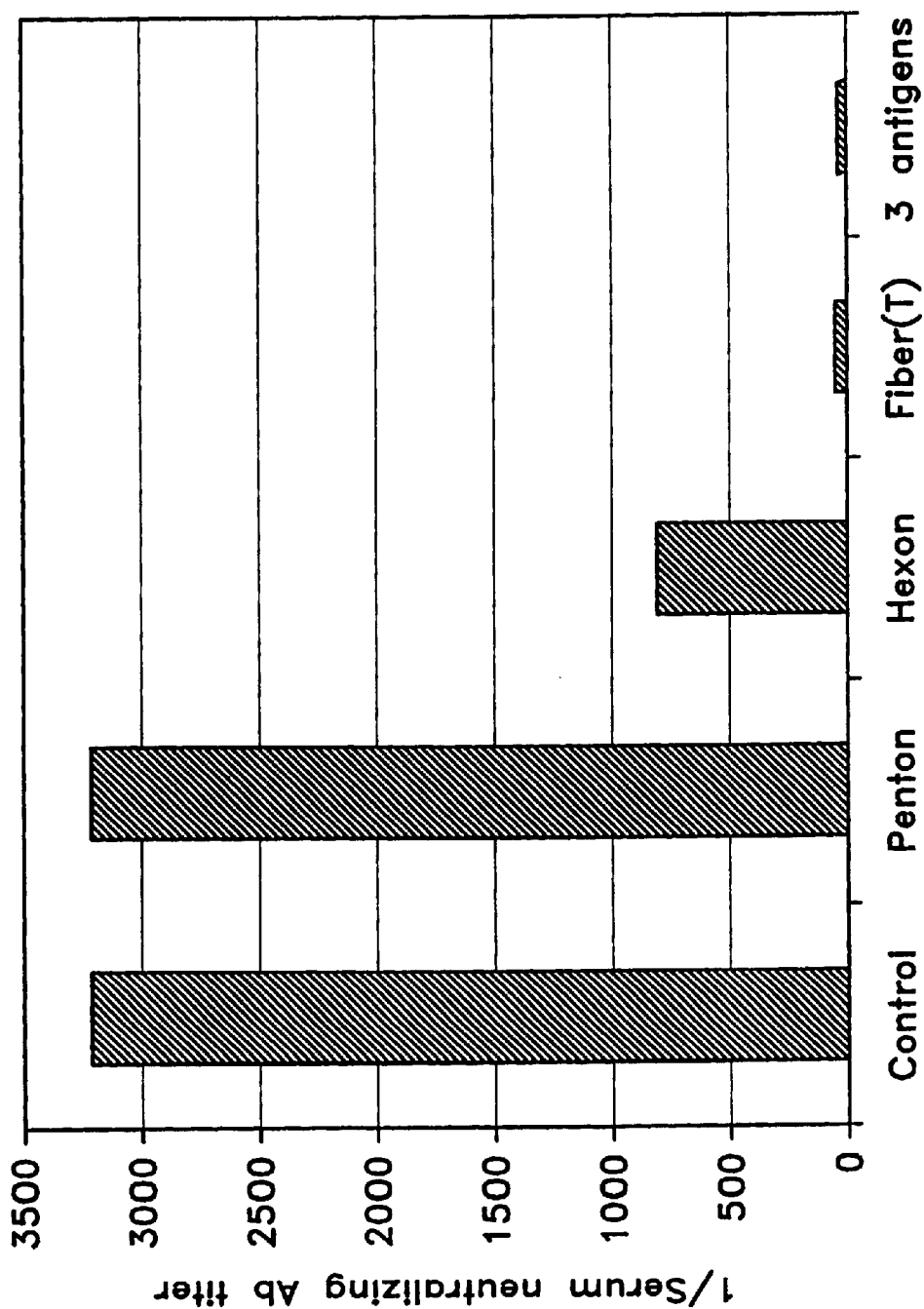
FIG. 20 is a graph depicting the relative efficiencies of various immunosorbents in clearing the neutralizing antibody activities present in GG/003.

The affinity columns containing recombinant hexon, fiber or penton proteins were prepared using methods known in the art in which the QIA column (see above) formed a basis for coupling the protein(s) to the matrix via the histidine tail. For each olumna, approximately 200 to 400 μg of protein (in about 1 ml) was mixed with about 0.5 ml of matrix. Experiments employing a combination of fiber, hexon, and penton proteins were performed by running three separate, sequential columns (with flow through from one column being loaded onto the next column). Whereas hexon- or penton-affinity columns cleared some of the antibodies reactive with their corresponding surface proteins (see FIGS. 15–16), more effective depletion of anti-adenovirus antibodies was observed when a combination of fiber, hexon, and penton proteins was used (FIGS. 18 and 20; Table 3). In particular, the combination approach was approximately 3 to 5 times more efficient in removing total anti-adenovirus antibodies present in normal human plasma with high pre-existing neutralizing antibody titer (FIG. 17). A similar result was observed when plasma collected from patients injected with CN706 was used (FIG. 19). It was estimated that the mixed affinity column depleted about 80% of the total anti-adenovirus antibodies and substantially eliminated the neutralizing activity from plasma.

TABLE 5

Relative Efficiencies of Various Immunosorbents in Clearing Either Neutralizing Antibody Activities (Nab titer) or Total Antiadenovirus Antibodies Present in Serum (GG/003) Derived from a Patient Who was treated with CN706

| GG/003(day 15) | Nab titer | Total anti-AD AB (ug/ml) |
|---|---|---|
| Neat | 1:3200 | 51.42 |
| Fiber (monomer) | 1:1600 | 22.24 |
| Fiber (trimer) | 1:25 or less | 10.95 |
| Fiber, penton, and hexon combination | 1:25 or less | 8.48 |

Figure 21:
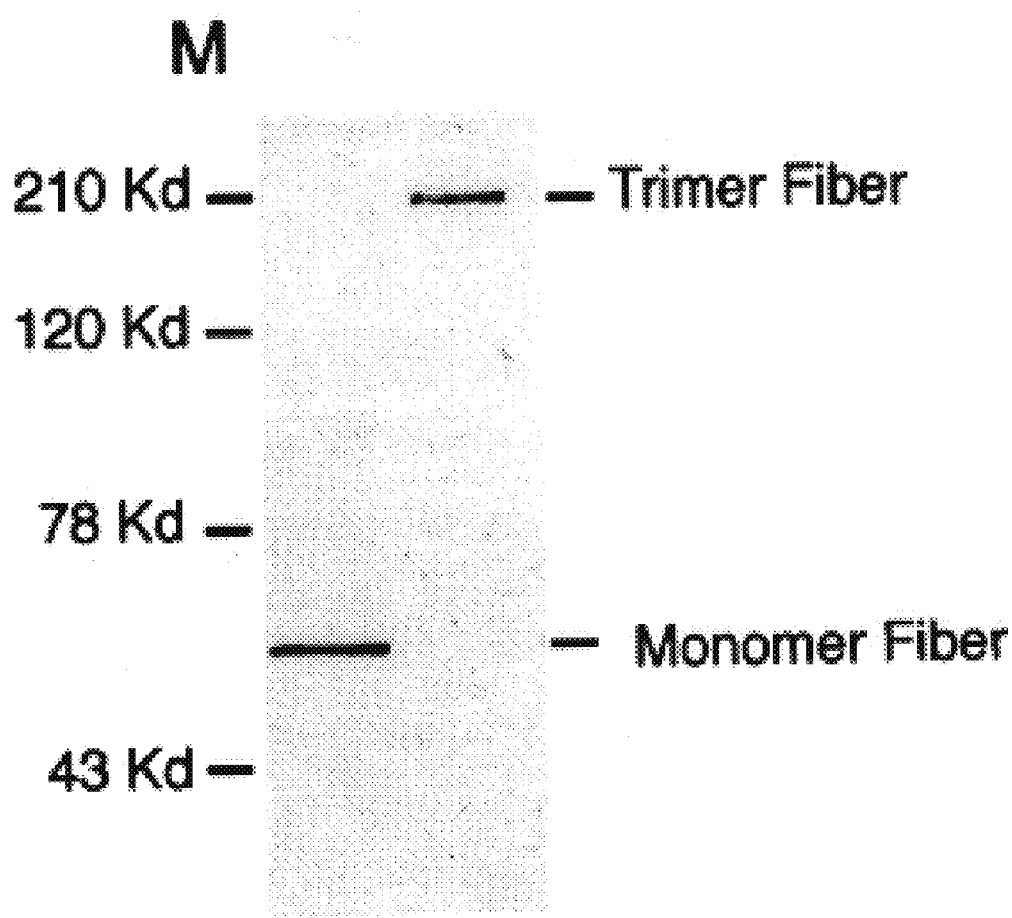
FIG. 21 is a reproduction of an immunoblot showing the assembly of trimeric adenovirus fiber protein from the monomers.
Figure 22:
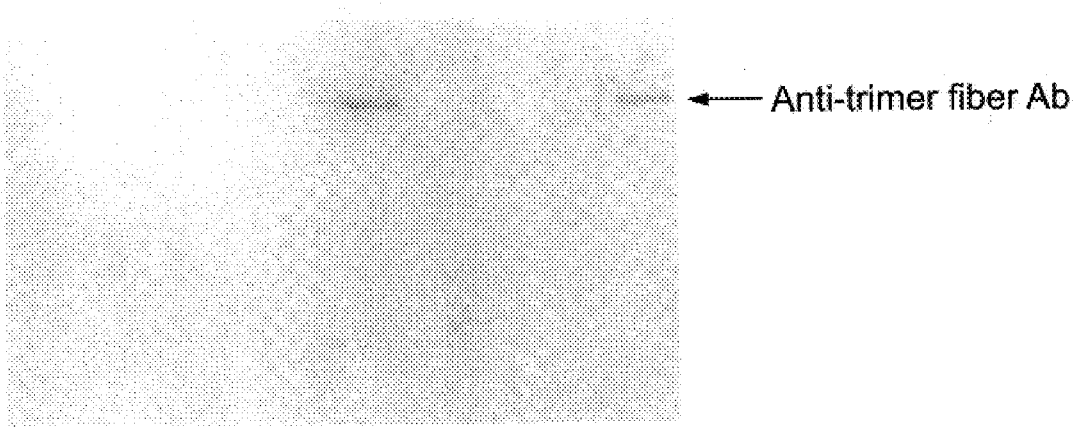
FIG. 22 is a reproduction of an immunoblot showing the depletion of anti-adenovirus trimer fiber antibodies from a patient's plasma using trimer-fiber affinity column.

We also observed that purified fiber proteins are able to reassemble to form a trimeric structure (FIG. 21). As shown in FIG. 22 and Table 5, the trimeric fiber serves as a better immunosorbent than a monomeric fiber. This result indicates the importance of fiber confirmation and/or configuration for recognition of the anti-fiber antibody. Taken together, our results show that adenovirus surface proteins, particularly fiber proteins, are effective in removing baseline anti-adenovirus antibodies as well as antibodies generated from secondary immune response.

Figure 9:
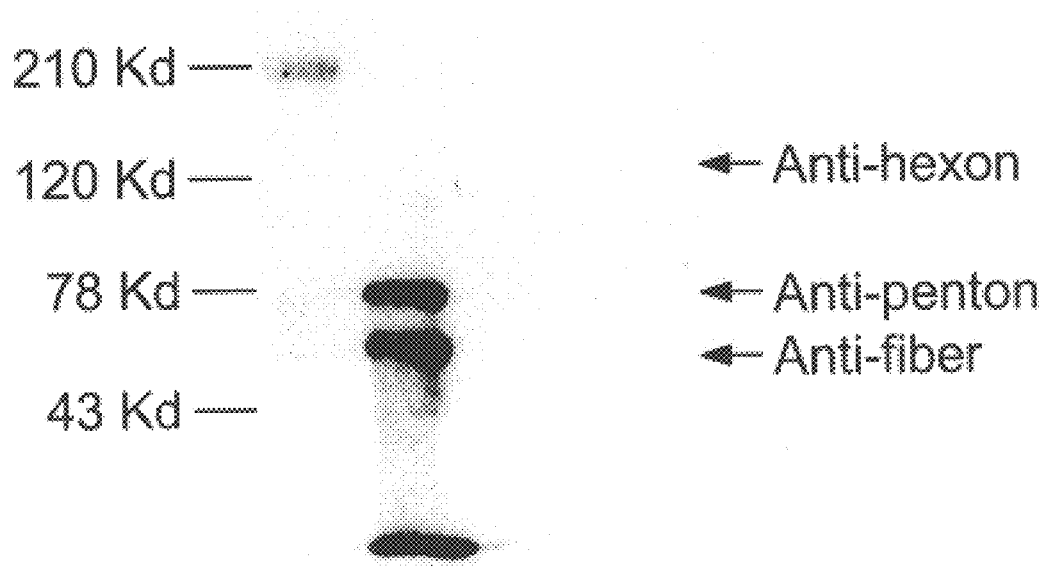
FIG. 9 is a reproduction of an immunoblot depicting the depletion of anti-adenovirus 5 antibodies from human plasma using a protein A affinity column. Whereas fractions 2 and 3 (F2, F3) do not contain antibodies capable of binding to adenovirus surface proteins hexon, penton and fiber, untreated plasma from the same individual contains antibodies reactive with these surface proteins as indicated by arrows.
Figure 10:
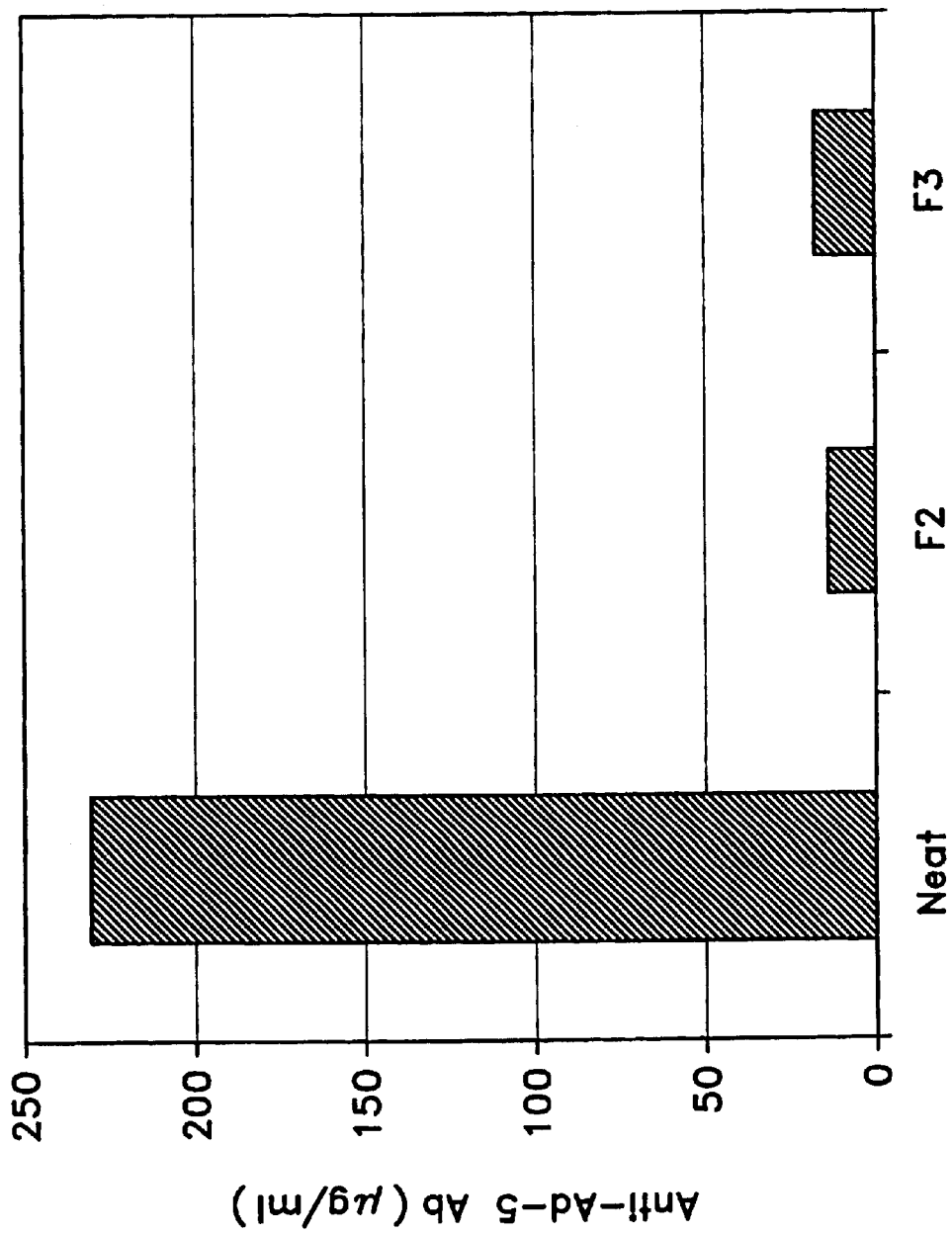
FIG. 10 is a bar graph depicting the removal of total anti-adenovirus 5 antibodies from human plasma using a protein A column. The lane "neat" represents the total anti-adenovirus 5 antibodies present in human plasma prior to protein A affinity chromatography. Lanes F2 and F3 show the anti-adenovirus 5 antibody concentrations of the second and third fractions collected from a protein A affinity column.
Figure 11:
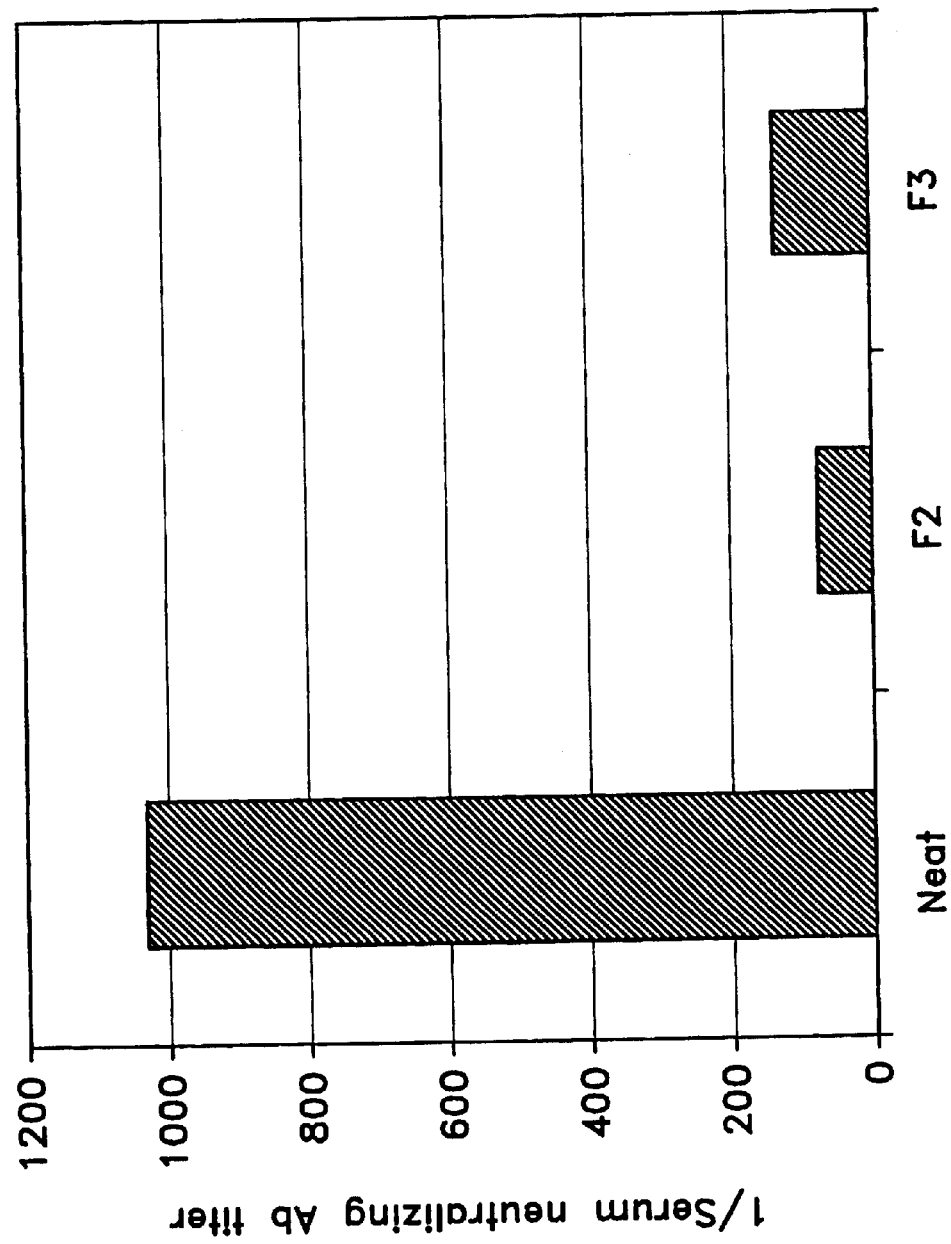
FIG. 11 is a graph depicting the removal of neutralizing antibodies activities from human plasma using a protein A column. "Neat" represents the neutralizing antibody activity present in human plasma prior to protein A affinity chromatography. F2 and F3 indicate the neutralizing antibody activities detected in the second and third fractions collected from a protein A affinity column.

The generic immunosorbent protein A, while being highly efficient in depleting anti-adenovirus antibodies present in human plasma (FIGS. 9–11), is generally not suitable for affinity adsorption apheresis. Protein A reacts with a wide spectrum of immunoglobulins ranging from IgG to IgM molecules and it presents a salient risk of suppressing patient's immune system. In particular, we found that protein A affinity column typically cleared 92% of IgG1 and IgG2, 70% of IgG4, and as much as 50% of IgG3 and IgM molecules present in patients' total plasma.

Example 4

Figure 23:
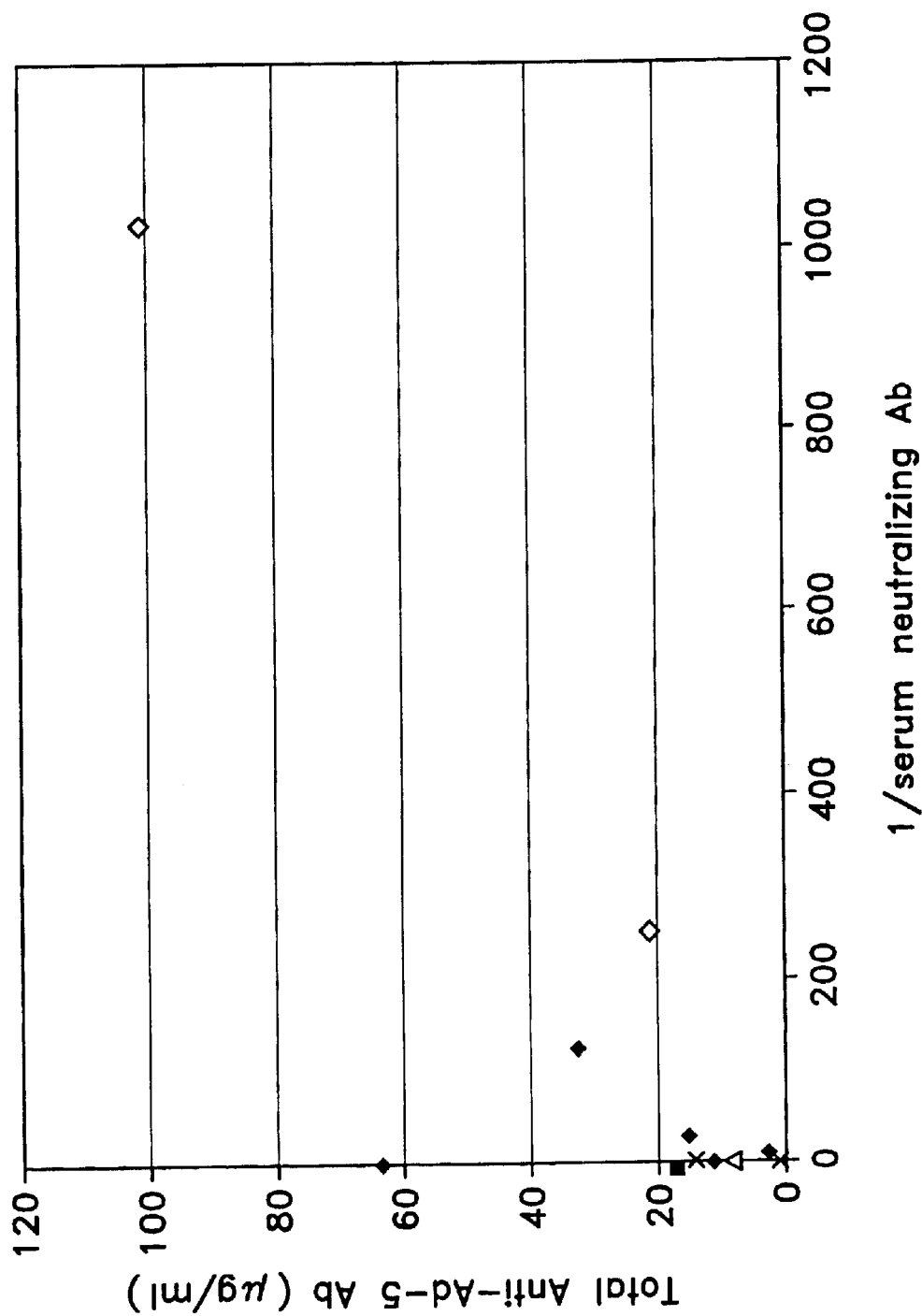
FIG. 23 is a graph showing the correlation of the amount of pre-existing neutralizing antibody activities and the amount of total anti-adenovirus 5 antibodies present in CN706 patients' plasma.
Figure 24:
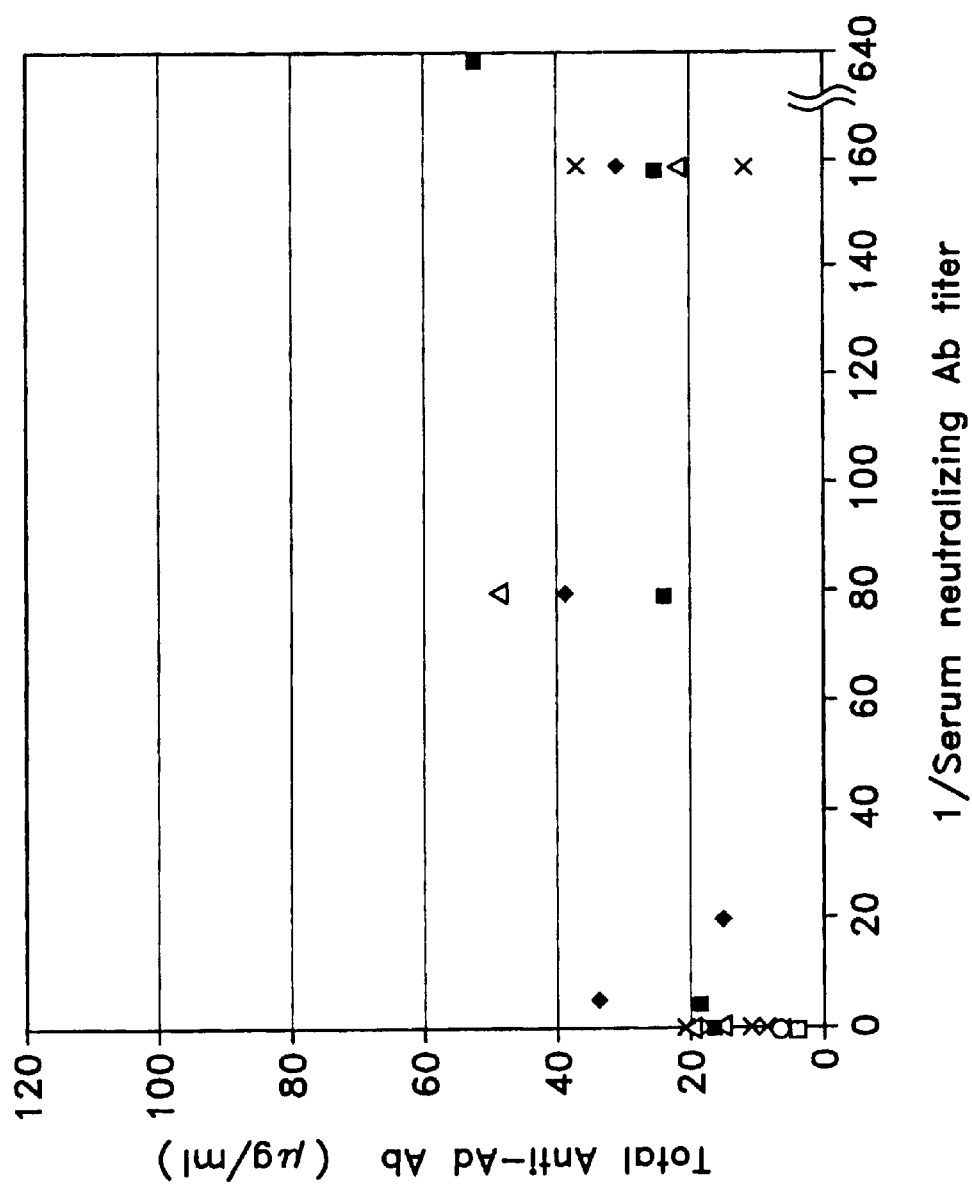
FIG. 24 is a graph showing the correlation of the amount of pre-existing neutralizing antibody activities and the amount of total anti-adenovirus 5 antibodies present in prostate cancer patients' plasma.

Determination of the Level of Patient's Pre-Existing Humoral Immunity to Viral Therapeutic Agents A statistical study involving approximately 40 patients revealed that about 95% of the patients having low or undetectable neutralizing antibody activity had an average total anti-adenovirus antibody content of less than 20 μg/ml (FIGS. 23 and 24). In this study, approximately ⅔ of the patients had prostate cancer, and the remaining ⅓ had also been treated with the therapeutic viral agent CN706 described herein. This data indicates that measuring anti-adenovirus antibody may be a reliable indicator of the degree of neutralizing antibody in an individual, permitting a more simplified assay system for detection and monitoring purposes.

Although the foregoing invention has been described in some detail by way of illustration and example for purposes of clarity of understanding, it will be apparent to those skilled in the art that certain changes and modifications can be practiced. Therefore, the description and examples should not be construed as limiting the scope of the invention, which is delineated by the appended claims.

What is claimed is:

1. A method of reducing pre-existing humoral immunity to a viral immunogenic therapeutic agent in an individual comprising treating the individual's blood extracorporeally with an immunosorbent that selectively binds anti-virus antibody to the viral therapeutic agent; removing antibody-immunosorbent complexes from the blood formed during the treatment, if any; and returning the blood to the individual.

2. The method of claim 1, wherein the viral immunogenic therapeutic agent is an adenovirus.

3. The method of claim 1, wherein the immunosorbent is an organic molecule.

4. The method of claim 1, wherein the immunosorbent is a polypeptide.

5. The method of claim 4, wherein the polypeptide is a viral surface protein.

6. The method of claim 5, wherein the surface protein is a capsid protein.

7. The method of claim 5, wherein the surface protein is a fiber protein.

8. The method of claim 5, wherein the surface protein is a penton protein.

9. The method of claim 1, wherein the immunosorbent is an antibody specific for the anti-virus antibody.

10. The method of claim 9, wherein the antibody is an anti-idiotype antibody.

11. The method of claim 2, wherein the immunosorbent is an adenovirus surface protein selected from the group consisting of hexon protein, fiber protein, penton protein, and any combination thereof.

12. The method of claim 11, wherein the immunosorbent comprises a mixture of adenovirus hexon protein, fiber protein, and penton protein.

13. The method of claim 11, wherein the fiber protein is trimeric.

14. The method of claim 2, wherein the individual's titer of neutralizing anti-virus antibody after treatment, expressed as the inverse of the lowest dilution required to produce complete inhibition of cytopathic effect in a standard neutralization assay, is not less than about 1:10.

15. The method of claim 2, wherein the individual's titer of neutralizing anti-virus antibody before treatment, expressed as the inverse of the lowest dilution required to produce complete inhibition of cytopathic effect in a standard neutralization assay, is at least about 1:10.

16. The method of claim 2, wherein the individual's titer of neutralizing anti-virus antibody before treatment, expressed as the inverse of the lowest dilution required to produce complete inhibition of cytopathic effect in a standard neutralization assay, is at least about 1:20.

17. The method of claim 2, wherein the total amount of anti-adenovirus antibody before treatment is greater than about 12 $\mu$g of antibody per 1 ml of serum.

18. A method of administering a viral therapeutic agent to an individual subject to a pre-existing humoral immunity to a viral immunogen, comprising the steps of:
   (a) treating the individual's blood extracorporeally with an immunosorbent that selectively binds anti-virus antibody;
   (b) removing antibody-immunosorbent complexes formed during the treatment, if any, from the blood;
   (c) returning the blood to the individual; and
   (d) administering the viral therapeutic agent to the individual.

19. The method of claim 18, wherein the immunosorbent is protein A.

20. The method of claim 18, wherein the immunosorbent is protein G.

21. The method of claim 18, wherein the antibody is IgG.

22. The method of claim 18, wherein the viral therapeutic agent is adenovirus.

23. The method of claim 1, further comprising administering at least one immunosuppressant.

24. The method of claim 1, further comprising administering at least one cytokine.

25. The method of claim 1, further comprising administering at least one cytokine and at least one immunosuppressant.

26. The method of claim 1, further comprising administering an anti-T cell receptor antibody.

* * * * *